(12) United States Patent
Campbell

(10) Patent No.: US 11,922,821 B2
(45) Date of Patent: *Mar. 5, 2024

(54) SYSTEMS AND METHODS FOR COLLECTING AND ANALYZING HAZARDOUS MATERIALS INFORMATION USING AN UNMANNED AERIAL VEHICLE

(71) Applicant: Alliance Solutions Group, Inc., Newport News, VA (US)

(72) Inventor: Robert K. Campbell, Yorktown, VA (US)

(73) Assignee: Alliance Solutions Group, Inc., Newport News, VA (US)

( * ) Notice: Subject to any disclaimer, the term of this patent is extended or adjusted under 35 U.S.C. 154(b) by 197 days.

This patent is subject to a terminal disclaimer.

(21) Appl. No.: 17/367,945

(22) Filed: Jul. 6, 2021

(65) Prior Publication Data

US 2021/0343168 A1 Nov. 4, 2021

Related U.S. Application Data

(63) Continuation of application No. 16/129,507, filed on Sep. 12, 2018, now Pat. No. 11,062,614.

(51) Int. Cl.
*G08G 5/00* (2006.01)
*B64C 39/02* (2023.01)
(Continued)

(52) U.S. Cl.
CPC ......... *G08G 5/0091* (2013.01); *B64C 39/024* (2013.01); *G06T 11/206* (2013.01);
(Continued)

(58) Field of Classification Search
CPC .................................................. G08G 5/0091
See application file for complete search history.

(56) References Cited

U.S. PATENT DOCUMENTS

| 5,724,255 A | 3/1998 | Smith et al. |
| 6,057,851 A | 5/2000 | Luken et al. |
(Continued)

FOREIGN PATENT DOCUMENTS

WO    WO 2017/2235331 A1    12/2017

OTHER PUBLICATIONS

2016 Emergency Response Guidebook, U.S. Department of Transportation, Pipeline and Hazardous Materials Safety Administration (2016) (400 pages).

(Continued)

*Primary Examiner* — Hyun D Park
(74) *Attorney, Agent, or Firm* — Ambrose, Mills & Lazarow, PLLC

(57) ABSTRACT

A computer-implemented method includes receiving a first input associated with an incident location of an incident. A second input associated with a measurement zone surrounding the incident location is received. The method further includes producing, via a display monitor, a set of waypoints associated with a flight path of an unmanned aerial vehicle (UAV) based on the first input and the second input. The set of waypoints is displayed on a satellite aerial map including the incident location.

20 Claims, 22 Drawing Sheets
(15 of 22 Drawing Sheet(s) Filed in Color)

(51) Int. Cl.
*G06T 11/20* (2006.01)
*B64U 101/30* (2023.01)
*B64U 101/35* (2023.01)
*G01N 33/00* (2006.01)

(52) U.S. Cl.
CPC ......... *G08G 5/0013* (2013.01); *G08G 5/0034* (2013.01); *B64U 2101/30* (2023.01); *B64U 2101/35* (2023.01); *G01N 2033/0093* (2013.01); *G06T 2210/61* (2013.01)

(56) References Cited

U.S. PATENT DOCUMENTS

| | | | |
|---|---|---|---|
| 6,295,859 B1 | 10/2001 | Hayden et al. | |
| 6,643,580 B1* | 11/2003 | Naimer | G08G 5/0034 |
| | | | 340/963 |
| 8,060,270 B2 | 11/2011 | Vian et al. | |
| 8,103,398 B2 | 1/2012 | Duggan et al. | |
| 9,679,539 B1* | 6/2017 | Kamath | G09B 29/102 |
| 9,747,809 B2 | 8/2017 | Levien et al. | |
| 2006/0075356 A1 | 4/2006 | Faulkner et al. | |
| 2011/0035149 A1 | 2/2011 | McAndrew et al. | |
| 2011/0130636 A1 | 6/2011 | Daniel et al. | |
| 2011/0213554 A1* | 9/2011 | Archibald | G01V 9/007 |
| | | | 702/6 |
| 2015/0145954 A1 | 5/2015 | Pulleti et al. | |
| 2016/0070265 A1* | 3/2016 | Liu | B64C 39/024 |
| | | | 701/25 |
| 2018/0209902 A1 | 7/2018 | Myshak et al. | |
| 2018/0284088 A1* | 10/2018 | Verbeck, IV | G01N 21/65 |
| 2020/0135036 A1 | 4/2020 | Campbell | |

OTHER PUBLICATIONS

Bartholmai, M., et al. "Micro-Drone for Gas Measurement in Hazardous Scenarios via Remote Sensing," Conference: Proceedings of the 6th WSEAS International conference on remote sensing (REMOTE '10)—Selected topics in power systems and remote sensing (2010), WSEAS Press, Iwate Prefectural University, Japan, Jan. 2010, pp. 149-152.

Capello, E., et al., "A Waypoint-Based Guidance Algorithm for mini UAVs," $2^{nd}$ IFAC Workshop on Research, Education and Development of Unmanned Aerial Systems, Nov. 2013, pp. 120-125.

Office Action for U.S. Appl. No. 16/129,507 dated Sep. 17, 2020.

Final Office Action for U.S. Appl. No. 16/129,507 dated Apr. 1, 2021.

* cited by examiner

SYSTEMS AND METHODS FOR COLLECTING AND ANALYZING HAZARDOUS MATERIALS INFORMATION USING AN UNMANNED AERIAL VEHICLE

CROSS-REFERENCE TO RELATED APPLICATIONS

This application is a continuation of U.S. patent application Ser. No. 16/129,507, entitled "Systems and Methods for Collecting and Analyzing Hazardous Materials Information Using an Unmanned Aerial Vehicle," filed Sep. 12, 2018, which is incorporated herein by reference in its entirety.

BACKGROUND

The embodiments described herein relate generally to systems and methods for collecting and analyzing information related to hazardous materials (or substances). More particularly, the embodiments described herein relate to systems and methods for generating and displaying flight paths for an unmanned aerial vehicle, manipulating emissions information collected from the unmanned aerial vehicle to validate spatial accuracy, and displaying the collected information on a satellite aerial map.

Unmanned aerial vehicles (UAVs) are vehicles that can carry cameras, sensors, communications devices, or other payloads, but that do not include any on-board human pilot. UAVs are often used to perform tasks in which the presence of an on-board human pilot is undesirable. For example, some known uses of UAVs include military reconnaissance flights, inspection of structures (e.g., inspection of bridges, dams, and buildings), and environmental monitoring. Most known UAVs are controlled by a remote pilot via a ground station, which can include a radio to transmit and receive signals from the UAV, a navigational screen to display vehicle information (e.g., altitude, heading, airspeed, etc.) to the remote pilot, and a control input to allow the remote pilot to input signals to control the operation of the UAV. Some known UAV ground stations include automated or semi-automated control systems that can adjust the flight path of the UAV or alert the pilot to avoid disturbances or obstacles within the desired area of flight. Such obstacles can include, for example, potentially hazardous topography (e.g., mountains), buildings, government restricted airspace, or other aircraft. Although known UAVs have been contemplated for use in assessing hazardous incidents, known control systems do not generate or update flight paths specific to the type of hazard (e.g., the type of chemical spilled), the environmental conditions (e.g., wind direction), and/or regulatory or recommended protective action procedures. For example, known methods for responding to a chemical spill include establishing various zones for hazard response teams. Such zones can include areas for evacuation, areas within which certain protective gear must be worn, and the like. Known UAV control systems, however, do not provide adequate flight plan mapping and flight path generation to efficiently evaluate the presence of hazardous materials (or substances) in such zones to support risk management decision making.

Additionally, because the operation of a UAV produces localized air disturbances, there are concerns that certain data collected (e.g., localized concentration of gas or biological matter) may not accurately represent the actual concentration or amount of a hazardous material (or substance) present at a particular location. Moreover, such concerns about data accuracy are magnified during procedures in which the UAV is moving while collecting data. Because of certain delays associated with hazard sampling, movement of the UAV can result in difficulties in determining the location corresponding to the collected data. Because UAVs have limited flight times (e.g., based on the available battery power), however, it is often desirable to move the UAV at the fastest possible speed to ensure that the maximum area is assessed. Thus, hovering the UAV during data collection is often not a desirable solution.

Thus, a need exists for systems and methods for generating and displaying flight paths for an unmanned aerial vehicle for use in collecting information about hazardous materials (or substances). Additionally, a need exists for systems and methods for manipulating the collected information to validate the spatial accuracy of the collected information. Further, a need exists for systems and methods for visually displaying the collected information on a satellite aerial map.

SUMMARY

System and methods for collecting and analyzing information related to hazardous materials are described herein. In some embodiments, a computer-implemented method includes receiving a first input associated with an incident location of an incident. A second input associated with a measurement zone surrounding the incident location is received. The method further includes producing, via a display monitor, a set of waypoints associated with a flight path of an unmanned aerial vehicle (UAV) based on the first input and the second input. The set of waypoints is displayed on a satellite aerial map including the incident location.

In some embodiments, a computer-implemented method includes receiving an emissions signal from an emissions sensor coupled to an unmanned aerial vehicle (UAV) and a position signal from a position sensor coupled to the UAV. The method then includes generating, via a georectification module and based on at least the position signal and a sensor response time, a set of geographic coordinates associated with the emissions signal. The georectification module can be implemented in at least one of a memory or a processing device of a UAV emissions display system. An emissions indicator based on the emissions signal and the set of geographic coordinates is then produced via a display monitor. The emissions indicator is displayed on a satellite aerial map.

In some embodiments, a computer-implemented method includes receiving a set of emissions data packets associated with an emissions sensor coupled to an unmanned aerial vehicle (UAV). Each emissions data packet includes at least an emissions signal from the emissions sensor, a position signal from a position sensor coupled to the UAV, an altitude of the UAV, and a time stamp. The method includes generating, via a georectification module and based on at least the position signal and a sensor response time, a set of geographic coordinates associated with each emissions data packet from the plurality emissions data packets. The set of emissions data packets is then filtered, via a graphics module, based a filter criterion. Each of the georectification module and the graphics module can be implemented in at least one of a memory or a processing device of a UAV emissions display system. The method then includes producing, via a display monitor, at least one emissions indicator based on an emissions data packet from the set emissions data packets and its set of geographic coordinates. The emissions indicator is displayed on a satellite aerial map and corresponds to one of the set of emissions data packets that satisfies the filter criterion.

BRIEF DESCRIPTION OF THE DRAWINGS

This application contains at least one drawing executed in color. Copies of this patent or patent application publication with color drawing(s) will be provided by the Office upon request and payment of the necessary fee.

DETAILED DESCRIPTION

Figure 1:
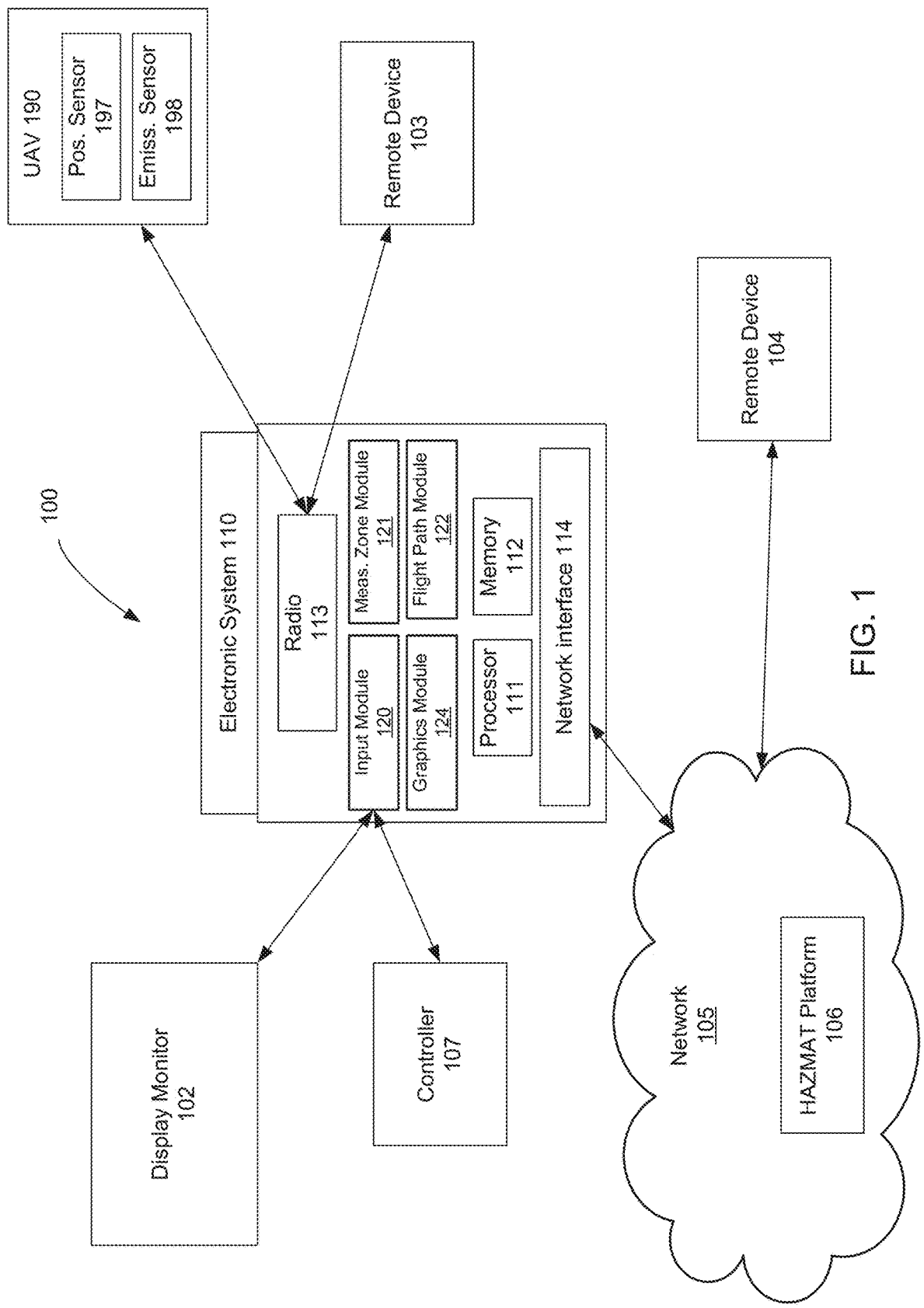
FIG. 1 is a schematic illustration of a control system for an unmanned aerial vehicle (UAV) according to an embodiment.

The control systems, display systems, and/or methods shown and described herein can be used with any suitable UAV to collect and analyze information related to hazardous incidents. Such hazardous materials or substances can include chemicals (e.g., from a chemical spill), gaseous emissions (e.g., from a fire or explosion), biological materials (e.g., from a biohazard release), radiation emissions (e.g., from a radioactive material or nuclear incident), or any other materials related to a hazardous incident. Hazardous incidents can include accidents, acts of terrorism, or even natural phenomenon (e.g., a volcanic eruption). The embodiments described herein can advantageously produce one or more flight paths to allow efficient data collection throughout various zones associated with the incident. The embodiments described herein also manipulate and/or filter the collected data to produce an accurate representation of the hazardous substance (e.g., gas concentration) along with a satellite aerial map (or image) of the incident location. In this manner, certain zones can be identified and properly sized to allow for the most efficient response to the incident. For example, the embodiments described herein can confirm, expand, or reduce the size of an isolation zone surrounding an incident to safely minimize the working distance between the emergency responders and the hazardous material (or substance). As another example, the data collected may be used to formulate response plans that are less conservative in the use of respiration equipment, protective equipment and the like. In turn, this can result in a more effective response to the hazardous incident.

In some embodiments, a computer-implemented method includes receiving a first input associated with an incident location of an incident. A second input associated with a measurement zone surrounding the incident location is received. The method further includes producing, via a display monitor, a set of waypoints associated with a flight path of an unmanned aerial vehicle (UAV) based on the first input and the second input. The set of waypoints is displayed on a satellite aerial map including the incident location.

In some embodiments, the method includes producing, via the display monitor, a measurement zone image representing the measurement zone. The measurement zone image is displayed on the satellite aerial map of the region and is scaled to the satellite aerial map to represent a size of the measurement zone. The measurement zone image can be an isolation zone image, a protective action zone image, or any other suitable zone associate with a hazardous incident. In some embodiments, the measurement zone image has an opacity such that the satellite aerial map can be viewed through the measurement zone image.

In some embodiments, the incident involves a hazardous substance. The second input includes an identification of the hazardous substance and an amount of the hazardous substance, which information can be received in response to an input prompt displayed via the display monitor. A size of the measurement zone can be determined automatically based on the information. Specifically, in some embodiments, the method further includes determining, via a measurement zone module implemented in at least one of a memory or a processing device of a UAV control system and based on the second input, the size of the measurement zone.

In some embodiments, the set of waypoints can be produced on the satellite map by first determining, via a flight path module implemented in at least one of a memory or a processing device of a UAV control system and based on a size and the incident location, a set of geographic coordinates for each waypoint. Next, the waypoints are displayed on the satellite aerial image based on the set of geographic coordinates for each waypoint. Further, the method can include determining, via the flight path module, a set of flight segments to define the flight path. Each flight segment connects at least two waypoints. The set of flight segments including a first flight segment between a first waypoint and a second waypoint and a second flight segment between the second waypoint and a third waypoint. The set of geographic coordinates for each waypoint is determined such that the first line segment intersects the incident location and the second flight segment is tangent to an isolation zone circle.

In some embodiments, the method includes determining, via the flight path module, a set of flight segments to define the flight path, with each flight segment connecting at least two waypoints. A flight distance based on the plurality of flight segments is then determined. The method further includes determining a minimum air speed threshold based on the flight distance and a flight duration. The flight duration can be, for example, limited based on the available battery power. The method further includes producing, via the display monitor, a notification associated with the minimum air speed.

In some embodiments, the method includes plotting at least one emissions indicator on the display monitor. For example, in some embodiments, the incident involves a hazardous substance and the UAV includes an emissions sensor and a position sensor. The emissions sensor is configured to produce an emissions signal associated with a concentration of the hazardous substance. The method can include receiving the emissions signal and information about the position of the UAV. The method further includes determining, via a georectification module implemented in at least one of a memory or a processing device of the UAV control system a set of geographic coordinates associated with the emissions signal. The geographic coordinates are determined based on at least a time stamp of the emissions signal, the position of the UAV, and a sensor response time. The emissions indicator is then displayed on the satellite aerial map based on the set of geographic coordinates.

In some embodiments, a computer-implemented method includes receiving a first input associated with an incident location of an incident involving a hazardous substance. A second input associated with a measurement zone including the incident location is received. A measurement zone image representing the measurement zone is then produced via a display monitor. The measurement zone image is displayed on a satellite aerial map of a region including the incident location. The measurement zone image is scaled to the satellite aerial map. The method further includes producing, via the display monitor, a flight path of an unmanned aerial vehicle (UAV) based on the first input and the second input. The flight path is displayed on the satellite aerial map of the region. The UAV including an emissions sensor configured to produce a signal associated with an amount of the hazardous substance.

In some embodiments, an apparatus includes a display monitor and a UAV control (or display) system operatively coupled to an unmanned aerial vehicle (UAV), which includes an emissions sensor and a position sensor. The UAV control system can control any of an air speed, an altitude or a position of the UAV. The UAV control system includes an input module, a measurement zone module, a flight path module, and a graphics module, each of which is implemented in at least one of a memory or a processing device of the UAV control system. The input module is configured to receive a first input and a second input. The first input is associated with an incident location of an incident involving a hazardous substance. The second input is associated with a measurement zone including the incident location. The measurement zone module is configured to generate a first set of geographic coordinates associated with a perimeter of the measurement zone based on the first input and the second input. The flight path module is configured to generate a second set of geographic coordinates associated with a flight path of the UAV based on the first input and the second input. The graphics module is configured to display via the display monitor A) a satellite aerial map of a region including the incident location, B) a measurement zone image representing the measurement zone, the measurement zone image displayed on the satellite aerial map, and C) the flight path displayed on the satellite aerial map. Each of the measurement zone image and the flight path are scaled to the satellite aerial map.

In some embodiments, the UAV control (or display) system further includes a sensor module and a georectification module, each of which is implemented in at least one of the memory or the processing device of the UAV control system. The sensor module is configured to receive an emissions signal from the emissions sensor and a position signal from the position sensor. The georectification module is configured to generate a third set of geographic coordinates associated with the emissions signal based on at least the position signal, and a sensor response time. The graphics module is configured to display via the display monitor an emissions indicator on the satellite aerial map based on the emissions signal and the third set of geographic coordinates. In some embodiments, the emissions indicator includes a color associated with a concentration of the hazardous material (or substance) based on the emissions signal.

In some embodiments, a non-transitory processor-readable medium includes code to cause a processor of a device to receive a first input and a second input. The first input is associated with an incident location of an incident involving a hazardous substance. The second input is associated with a measurement zone including the incident location. The non-transitory processor-readable medium includes code to generate a first set of geographic coordinates associated with a perimeter of the measurement zone based on the first input and the second input. The non-transitory processor-readable medium includes code to generate a second set of geographic coordinates associated with a flight path of the UAV based on the first input and the second input. The non-transitory processor-readable medium includes code to display via a display monitor A) a satellite aerial map of a region including the incident location, B) a measurement zone image representing the measurement zone, the measurement zone image displayed on the satellite aerial map, and C) the flight path displayed on the satellite aerial map. Each of the measurement zone image and the flight path are scaled to the satellite aerial map.

In some embodiments, a computer-implemented method includes receiving an emissions signal from an emissions sensor coupled to an unmanned aerial vehicle (UAV) and a position signal from a position sensor coupled to the UAV. The method then includes generating, via a georectification module and based on at least the position signal and a sensor response time, a set of geographic coordinates associated with the emissions signal. The georectification module can be implemented in at least one of a memory or a processing device of a UAV emissions display system. An emissions indicator based on the emissions signal and the set of geographic coordinates is then produced via a display monitor. The emissions indicator is displayed on a satellite aerial map.

In some embodiments, the emissions signal is associated with a concentration of a hazardous material (or substance) detected by the emissions sensor. The operation of producing the emissions indicator can include first selecting a color associated with the concentration of the hazardous material (or substance), and second producing the color within an emissions area of the display monitor. In some embodiments, the emissions area is scaled to represent a region on the satellite aerial map corresponding to the concentration of the hazardous material (or substance). In some embodiments, the color is selected from a color scale representing a range of exposure safety levels associated with the concentration of the hazardous material (or substance). In some embodiments, the generating the set of geographic coordinates is based on an air speed of the UAV.

In some embodiments, an apparatus includes a display monitor and a UAV missions display (or control) system operatively coupled to an unmanned aerial vehicle (UAV), which includes an emissions sensor and a position sensor. The UAV emissions display system includes a sensor module, a georectification module, and a graphics module, each of which is implemented in at least one of a memory or a processing device of the UAV emissions display system. The sensor module is configured to receive an emissions signal from the emissions sensor and a position signal from the position sensor. The georectification module is configured to generate a set of geographic coordinates associated with the emissions signal based on at least the position signal and a sensor response time. The graphics module is configured to display via the display monitor an emissions indicator on a satellite aerial map based on the emissions signal and the set of geographic coordinates.

In some embodiments, a non-transitory processor-readable medium includes code to cause a processor of a device to receive an emissions signal from an emissions sensor coupled to a UAV and a position signal from a position sensor coupled to the UAV. The non-transitory processor-readable medium includes code to generate a set of geographic coordinates associated with the emissions signal based on at least the position signal and a sensor response time. The non-transitory processor-readable medium includes code to display, via a display monitor, an emissions indicator on a satellite aerial map based on the emissions signal and the set of geographic coordinates.

In some embodiments, a computer-implemented method includes receiving a set of emissions data packets associated with an emissions sensor coupled to an unmanned aerial vehicle (UAV). Each emissions data packet includes at least an emissions signal from the emissions sensor, a position signal from a position sensor coupled to the UAV, an altitude of the UAV, and a time stamp. The method includes generating, via a georectification module and based on at least the position signal and a sensor response time, a set of geographic coordinates associated with each emissions data packet from the plurality emissions data packets. The set of emissions data packets is then filtered, via a graphics module, based a filter criterion. Each of the georectification module and the graphics module can be implemented in at least one of a memory or a processing device of a UAV emissions display system. The method then includes producing, via a display monitor, at least one emissions indicator based on an emissions data packet from the set emissions data packets and its set of geographic coordinates. The emissions indicator is displayed on a satellite aerial map and corresponds to one of the set of emissions data packets that satisfies the filter criterion.

The term "about" when used in connection with a referenced numeric indication means the referenced numeric indication plus or minus up to 10% of that referenced numeric indication. For example, "about 100" means from 90 to 110.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. Such non-parallelism or slight deviations can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

As used herein, the term "set" can refer to multiple features or a singular feature with multiple parts. For example, when referring to set of coordinates, the set of coordinates can be considered as one unit or be considered as multiple, distinct portions (e.g., a longitude coordinate and a latitude coordinate).

As used herein, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or graphic representation in addition to the position and orientation shown in the figures. For example, if a graphical depiction in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations.

As used herein, the term "measurement zone" can refer to any region, area, or volume for which measurements or information is desired. A measurement zone can a two-dimensional area defined, for example, by latitude and longitude points or a three-dimensional volume that includes a height (or altitude) dimension. Further, although specific types of measurement zones (e.g., an isolation zone or a protective action zone) are described herein, a measurement zone can be any defined region, area, or volume, and need not conform to any particular size, shape, or dimensions.

As used herein, the terms "hazardous substance" and "hazardous material" are used to refer to any substance or item that can present a hazard. Thus, either a "hazardous substance" or a "hazardous material" can refer to any item (biological, chemical, radiological, and/or physical), which has the potential to cause harm to humans, animals, or the environment, either by itself or through interaction with other factors.

FIG. 1 is a schematic illustration of a UAV control (or display) system 100 (also referred to herein simply as "the system 100") according to an embodiment. The system 100 is designed to operate and/or interface with a UAV 190. The UAV can be any aerial vehicle that does not include any on-board human pilot. Specifically, the UAV 190 can be any vehicle of the types shown and described herein, including the UAV 590 described below. As shown, the UAV includes a position sensor 197 and an emissions sensor 198. The position sensor 197 can be any sensor (or group of sensors) that produces one or more signals associated with any of the position, velocity, and orientation of the UAV 190. For example, in some embodiments, the position sensor 197 (or any of the position sensors described herein) can include an inertial navigation system (INS) that uses a global positioning sensor (GPS), accelerometers, gyros and magnetometers to estimate position and velocity of the UAV. The position sensor 197 (or any of the position sensors described herein) can also include one or more sensors (or components) to measure the altitude of the UAV 190. For example, in some embodiments, the position sensor 197 (or any of the position sensors described herein) can include any of a GPS, an air pressure altimeter (which can be integrated within INS system), and an ultrasonic range finder. The emissions sensor 198 can be any sensor (or group of sensors) that produces one or more signals associated with an amount, concentration, or presence of a material. For example, any of the emissions sensors described herein can include any suitable chemical, biological, or radiation (CBR) sensor. Specifically, the emissions sensor 198 (and any of the sensors described herein) can include a gas sensor that produces a signal associated with a concentration of a chemical gas. Such sensors can detect, for example, carbon monoxide, hydrogen sulfide, volatile organic compounds (e.g., via a photoionization detector), pentane, butane, octane, ammonia, chlorine, a Lower Explosive Limit (LEL) sensor, or any other chemical of interest. In some embodiments, the emissions sensor 198 (and any of the sensors described herein) can include a radiation sensor. Such radiation sensors can quantify and/or identify isotopes. In some embodiments, the emissions sensor 198 (and any of the sensors described herein) can include a sensor that produces a signal associated with the presence of a biological material (e.g., pathogen).

As shown, the system 100 includes a display monitor 102 and an electronic circuit system 110. The system 100 can optionally include a controller 107 and can optionally be operatively coupled to a first remote device 103 and a second remote device 104. As described in more detail below, the second remote device 104 can be coupled to the electronic circuit system 110 via a network 105. The UAV control (or display) system 100 is configured to perform any of the methods described herein, including controlling the flight path of the UAV 190, generating one or more flight paths, receiving and graphing emissions data, and processing the data for more efficient viewing and storage.

In some embodiments, the display monitor 102 and the electronic circuit system 110 can be a laptop computer, in which the display monitor 102 is integrated with the electronic circuit system 110. In other embodiments, the display monitor 102 can be a separate device that is spaced apart from (but operatively coupled to) the electronic circuit system 110. The display monitor 102 can be any suitable monitor or screen that displays visual elements to a user. The display monitor 102 can be a touch screen (of a smart mobile phone, tablet, or other device) upon which a series of graphical user interface elements (e.g., windows, icons, input prompts, graphical buttons, data displays, notification, or the like) can be displayed. In some embodiments, the system 100 can include multiple display monitors. For example, one display monitor 102 can be present near the controller 107 and/or the electronic circuit system 110 to assist the remote pilot in operating the UAV 190. A second display monitor (e.g., the remote device 104) can be at a remote location and can be used by emergency personnel to assess the status of the hazardous incident. Such remote display monitors can receive information from a HAZMAT computing platform 106, which is operatively coupled to the electronic circuit system 110 via the network 105.

The electronic circuit system 110 can be any suitable computing device or set of devices to perform the functions described herein. In some embodiments, the electronic circuit system 110 can be a specialized UAV control computer, or the like. The electronic circuit system 110 includes a processor 111, a memory 112, a radio 113, and a network interface 114. The electronic circuit system 110 also includes an input module 120, a measurement zone module 121, a flight path module 122, and a graphics module 124. Although shown as including each of the input module 120, the measurement zone module 121, the flight path module 122, and the graphics module 124, in other embodiments an electronic circuit system need not include all (or any) of these modules, and can include any other modules described herein, such as a georectification module, (e.g., the georectification module 223 described with respect to FIG. 8) and/or a sensor module (e.g., the sensor module 225 described with respect to FIG. 8). Moreover, although shown as including a series of components within one device, in other embodiments, the electronic circuit system 110 can include certain portions in one device (and at one location) and other portions in another device (and at another location). For example, in some embodiments, the electronic circuit system 110 can include the radio 113 in one device near the incident location and one or more of the application modules (e.g. the flight path module 122) in a second, separate device that is remotely located.

The processor 111, and any of the processors described herein (including the processor 211 described below), can be any suitable processor for performing the methods described herein. In some embodiments, processor 111 can be configured to run and/or execute application modules, processes and/or functions associated with the system 100. For example, the processor 111 can be configured to run and/or execute the input module 120, the measurement zone module 121, the flight path module 122, and the graphics module 124, and/or any of the other modules described herein, and perform the methods associated therewith. The processor 111 can be, for example, a Field Programmable Gate Array (FPGA), an Application Specific Integrated Circuit (ASIC), a Digital Signal Processor (DSP), and/or the like. The processor 111 can be configured to retrieve data from and/or write data to memory, e.g., the memory 112. In some embodiments, the processor 111 can cooperatively function with the radio 113 and/or execute instructions from code to provide signals to communicatively couple the electronic circuit system 110 to the UAV 190 and/or the remote device 103 (e.g., via wireless communication). In some embodiments, the processor 111 can cooperatively function with the network interface 114 and/or execute instructions from code to provide signals to communicatively couple the electronic circuit system 110 to the network 105 and the HAZMAT platform 106.

The memory 112 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 112 stores instructions to cause the processor 111 to execute modules, processes and/or functions associated with the system 100 and/or the UAV 190. For example, the memory 112 can store instructions to cause the processor 111 to execute one or more of the input module 120, the measurement zone module 121, the flight path module 122, and the graphics module 124, and perform the methods associated therewith.

The radio 113 (also referred to as a receiver, transmitter and/or transceiver) can be operable to send signals to, and/or receive radio signals, such as Bluetooth®, ZigBee, Wi-Fi, cellular telephone signals, etc. In some embodiments, the radio 113 can be integral with the processor 111. In other embodiments, the radio 113 can include a processor distinct from the processor 111. In some embodiments, the radio 113 can be operable to communicatively couple (also referred to herein as "linking" or "pairing") the electronic circuit system 110 to the UAV 190 and/or the remote computing device 103. The remote computing device 103 can be, for example, a device that measures and transmits environmental data (e.g., wind speed, wind direction, temperature, or the like). For example, in some embodiments, the remote computing device 103 can be a computing device employed by an emergency response team.

The input module 120 can be a hardware and/or software module (stored in memory 112 and/or executed in the processor 111). As described in more detail herein, the input module 120 is configured to receive one or more inputs related to a hazardous incident. The input module 120 can receive the inputs in any suitable manner. For example, in some embodiments, the input module 120 can receive one or more inputs in response to an input prompt displayed on the display monitor 102. For example, in some embodiments inputs related to the sensor setup, incident site, or the like can be entered in response to prompts presented via a HAZMAT input menu (see e.g., the HAZMAT input window 440 shown and described below with reference to FIG. 11). In other embodiments, the input module 120 can receive one or more inputs from the remote device 103 and/or the remote device 104. For example, in some embodiments, inputs related to local wind direction, temperature, and time of day can be received directly from either remote device. In this manner, the inputs can be received with limited manual input, thereby improving accuracy and efficiency of receiving the inputs.

In some embodiments, the input module 120 can receive a first input associated with an incident location and a second input associated with a measurement zone including the incident location. The first input can be, for example, a street address of the incident location, a set of geographic coordinates associated with the incident location, a name of the incident location, or any other identifying information about the incident location. The first input can be received, for example, in response to the incident site input prompt 443 shown and described herein. In some embodiments, the second input can include a type of measurement zone. For example, response guidelines can provide for the identification of multiple different zones within which (or related to which) different activities will be undertaken to mitigate the negative effects of the hazardous incident. Such zones can include, for example, an isolation zone, which is an area surrounding the incident location within which a person may be exposed to dangerous or life-threatening concentrations of materials, or a protective action zone, which is an area downwind of the incident site distance within which person may become incapacitated or incur serious or irreversible health effects. Accordingly, in some embodiments, the second input can include a selection of whether the emissions measurements are to be taken within an isolation zone or a protective action zone. Such inputs can be received, for example, in response to the isolation zone input prompt 444 or the protective action zone input prompt 445 shown and described herein.

In some embodiments, the second input can include a size associated with the measurement zone. For example, in some embodiments, the second input can be a radius of a circle that defines an isolation zone about the incident site. In other embodiments, the second input can be a downwind distance that defines a protective action zone about the incident site. Such distances can be received by the input module 120 via drop-down menus that allow for efficient selection of commonly used distances. Such distances can be consistent with those set forth in the North American Emergency Response Guidebook. In other embodiments, however, the second input can be information from which such sizes can be determined. For example, in some embodiments, the second input can include any of an identification of the hazardous substance, an amount of the hazardous substance, a wind direction, and a time of day. Certain portions of this information can be received in response to one or more prompts, and other portions of this information can be received directly from one or more remote devices. As one example, in some embodiments, the second input can include a chemical identification number (e.g., ID No. 1017 for chlorine gas), a name of the chemical (e.g., chlorine), an amount of the chemical (e.g., whether the incident involves more or less than 55 gallons), and the time of day (to evaluate whether current conditions are considered as day or night). Based on this information, the electronic circuit system 110 (e.g., the measurement zone module) can determine the appropriate measurement zone distance that is specific to the hazardous incident and acceptable risk of exposure.

The measurement zone module 121 can be a hardware and/or software module (stored in memory 112 and/or executed in the processor 111). As described in more detail herein, the measurement zone module 121 is configured to produce one or more sizes, geographic coordinates, or locations associated with the selected measurement zone to facilitate producing an accurate measurement zone image that represents the desired measurement zone at the incident site. For example, in some embodiments, as described above, the measurement zone module 121 is configured to receive either or both of the first input and the second input and determine a size associated with the measurement zone. For example, in some embodiments, the measurement zone module 121 can determine, based on a chemical identification number and an amount of the chemical, the radius of an isolation zone. In other embodiments, the measurement zone module 121 can determine, based on a chemical identification number, an amount of the chemical, and the time of day, a downwind distance of a protective action zone. Such determinations can be performed by a table look-up, a calculation, or any other suitable method. In some embodiments, for example, the downwind distance can be determined based on additional inputs, such as wind speed, temperature, wind direction, or the like, and can be based on plume modeling calculations.

Figure 3:
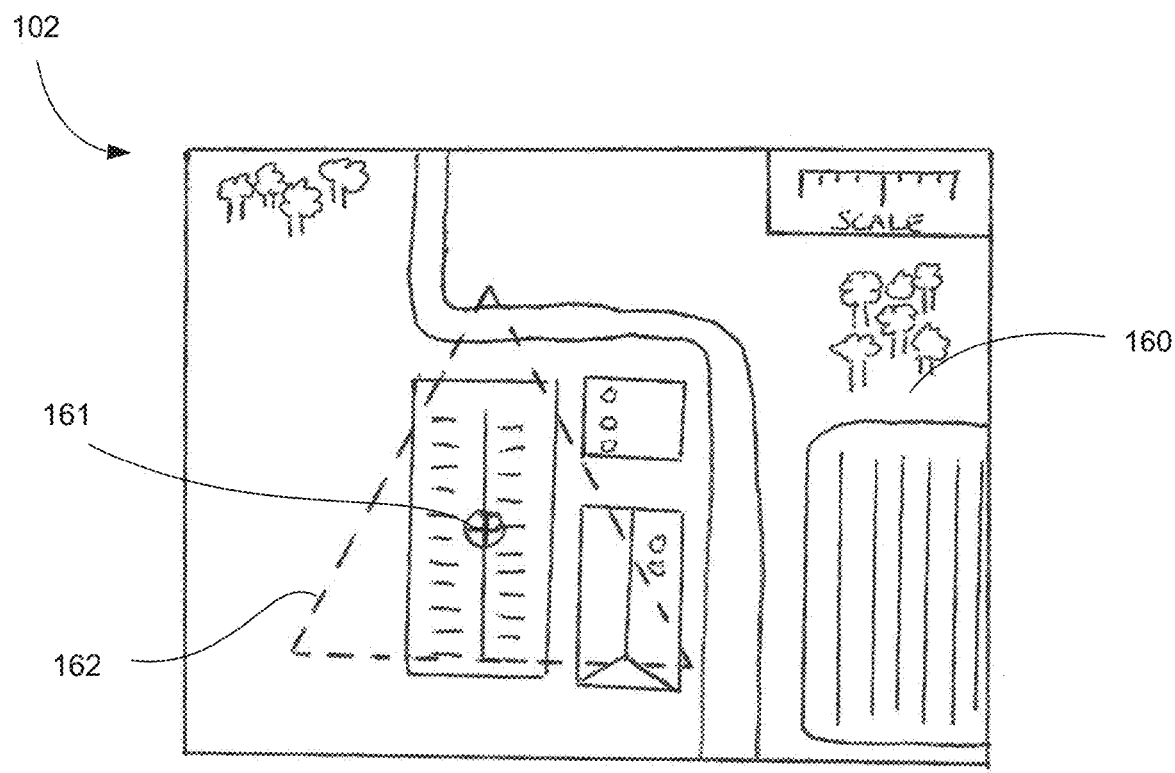
FIGS. 3-6 depict the display of one or more flight path waypoints on a satellite aerial map produced by the control system shown in FIG. 1 or according to the method shown in FIG. 2.
Figure 5:
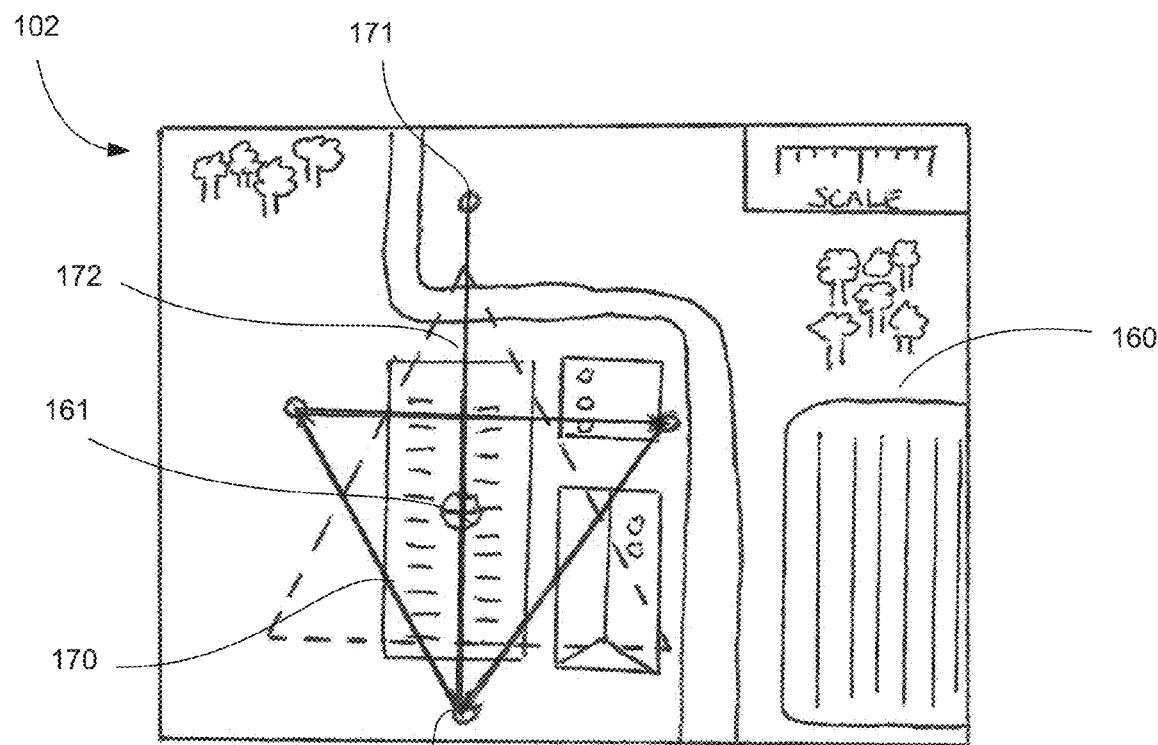
Figure 6:

In some embodiments, the measurement zone module 121 is configured to generate a set of geographic coordinates associated with a perimeter of the measurement zone based on the first input and the second input. For example, in some embodiments, a measurement zone can be defined by a circle about the incident site, a series of line segments (or arcs) about the incident site, or any combination of these. Referring to FIG. 3, the measurement zone image 162 is a set of line segments about the incident site 161. To enable an accurate graphical display of the measurement zone image 162 (or compilation of a data file for later use), the measurement zone module 121 can produce one or more sets of geographic coordinates (e.g., longitude and latitude) that identify one or more points on the measurement zone. In some embodiments, the measurement zone module 121 is configured to determine such coordinates based in part on the wind direction. For example, FIG. 5 shows the measurement zone image and the flight path 170 in a first orientation. FIG. 6 shows the wind direction indicated by the arrow AA. As shown, the flight path 170 is rotated as shown by the arrow BB to be oriented or aligned with the wind direction.

Figure 4:
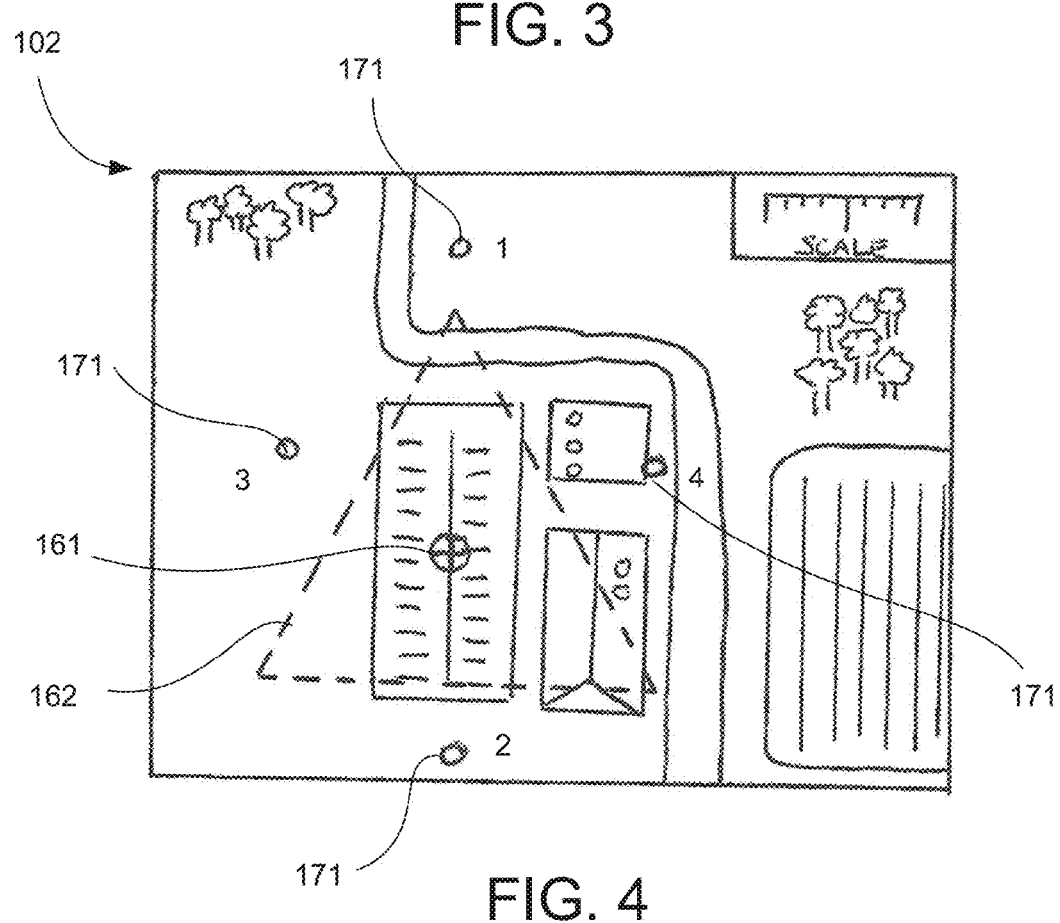

The flight path module 122 can be a hardware and/or software module (stored in memory 112 and/or executed in the processor 111). As described in more detail herein, the flight path module 122 is configured to generate a flight path of the UAV. The flight path can be generated based on the first and second inputs (e.g., the selection and definition of the measurement zone), type of emissions survey desired (e.g., an isolation zone survey, a downwind hazard survey, or the like), the desired time (or maximum distance) for completing the measurements, or the like. For example, in some embodiments, the flight path module 122 is configured to generate a set of waypoints for the flight path. For example, FIG. 4 shows a set of four waypoints 171 displayed on satellite aerial map (or image) 160 shown on the display monitor 102. In some embodiments, the flight path module 122 can generate a set of geographic coordinates for each waypoint. In some embodiments, the flight path module 122 can generate a set of flight segments to define the flight path. For example, referring to FIG. 5, the flight path module 122 can generate a set of flight segments 172 (only one flight segment is identified) between the waypoints 171 to define the flight path 170. As shown, each flight segment connecting at least two waypoints. As described in more detail below, the flight path module 122 is configured to generate the waypoints such that the flight segments and/or the flight path traverses the desired portions of the measurement zone (e.g., along an upwind edge of the measurement zone, directly through the incident site within the measurement zone, or the like).

In some embodiments, the flight path module 122 is configured to determine the flight path (and/or the waypoints) based in part on the wind direction. For example, FIG. 5 shows the flight path 170 including a flight segment 171 in a first orientation. FIG. 6 shows the wind direction indicated by the arrow AA. As shown, the flight path 170 is rotated as shown by the arrow BB to be oriented or aligned with the wind direction. Similarly stated, in some embodiments, the flight path module 122 is configured to generate a set of geographic coordinates for each waypoint of the flight path such that a flight segment is aligned with the wind direction.

In some embodiments, the flight path module 122 is configured to determine the total flight distance associated with the flight path. The flight path module 122 can determined, based on the total flight distance, a minimum air speed threshold. For example, in some embodiments, the total flight time for the UAV 190 can be 20 minutes (based on a known battery charge level). The minimum air speed threshold, therefore, is the total flight distance divided by the total flight time (e.g., 20 minutes). In some embodiments, a notification associated with the minimum air speed can be produced on the display monitor 102. In this manner, the remote pilot can be aware of a desired minimum speed, can be notified if the current speed drops below the minimum speed, or the like.

The graphics module 124 can be a hardware and/or software module (stored in memory 112 and/or executed in the processor 111). As described in more detail herein, the graphics module 124 is configured to display a set of images on the display monitor 102 to facilitate the emissions data sampling by the UAV 190, evaluations of the received emissions data, and the like. Specifically, the graphics module 124 is configured to display a satellite aerial map of a region including the incident location. For example, referring to FIG. 3, the graphics module can display a satellite aerial map 160 of a region that includes the incident location 161. The graphics module 124 is also configured to display a measurement zone image representing the measurement zone. For example, FIG. 3 shows the measurement zone image 162 displayed on the satellite aerial map 160. The graphics module 124 is also configured to display the flight path and/or a series of waypoints on the satellite aerial map. For example, referring to FIG. 5, the graphics module can display the flight path 170 on the satellite aerial map 160. Moreover, each of the measurement zone image and the flight path are scaled to the satellite aerial map to accurately represent the size of these images.

In some embodiments, the graphics module 124 is configured to display one or more emissions indicators on the satellite aerial map to graphically depict the measured emissions.

In some embodiments, the graphics module 124 is configured to adjust the characteristics of the measurement zones, flight paths, and emissions indicators graphed. For example, in some embodiments any of these items can be displayed with an opacity such that portions of the underlying satellite image can be viewed. For example, in some embodiments, an isolation zone image has a first color and a first opacity such that the satellite aerial map can be viewed through the isolation zone image, while a protective action zone image has a second color and a second opacity such that the satellite aerial map can be viewed through the protective action zone image.

The network 105 can be a piconet, the Internet, an intranet, a local area network (LAN), a wide area network (WAN), a virtual network, a telecommunications network, any other suitable communication system and/or combination of such networks. The network 105 can be implemented as a wired and/or wireless network.

The HAZMAT platform 106 can be any suitable computer-implemented interface and/or computing entity, such as a server or personal computer, that is configured to communicate with the electronic circuit system 110, the remote device 104, and/or the remote device 103, and/or any other portions of the system 100. More specifically, the HAZMAT platform 106 can receive information from devices within the system 100, manipulate the information, and produce information to any of the devices within the system 100. For example, in some embodiments, emissions information collected by the UAV 190 can be transmitted from the electronic circuit system 110 to the HAZMAT platform 106. The HAZMAT platform 106 can then send notifications, via the network 105 to the remote computing device 104, which can be associated with an emergency response team.

The remote device 103 and the remote device 104 can be any suitable computing entity, such as a server, personal computer, tablet device, or mobile computing device. In some embodiments, the remote device 103 and/or the remote device 104 can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), and/or any other suitable computing entity. As described above, the remote computing device 103 can be, for example, a device that measures and transmits environmental data (e.g., wind speed, wind direction, temperature, or the like). For example, in some embodiments, the remote computing device 103 can be a computing device employed by an emergency response team.

Figure 2:
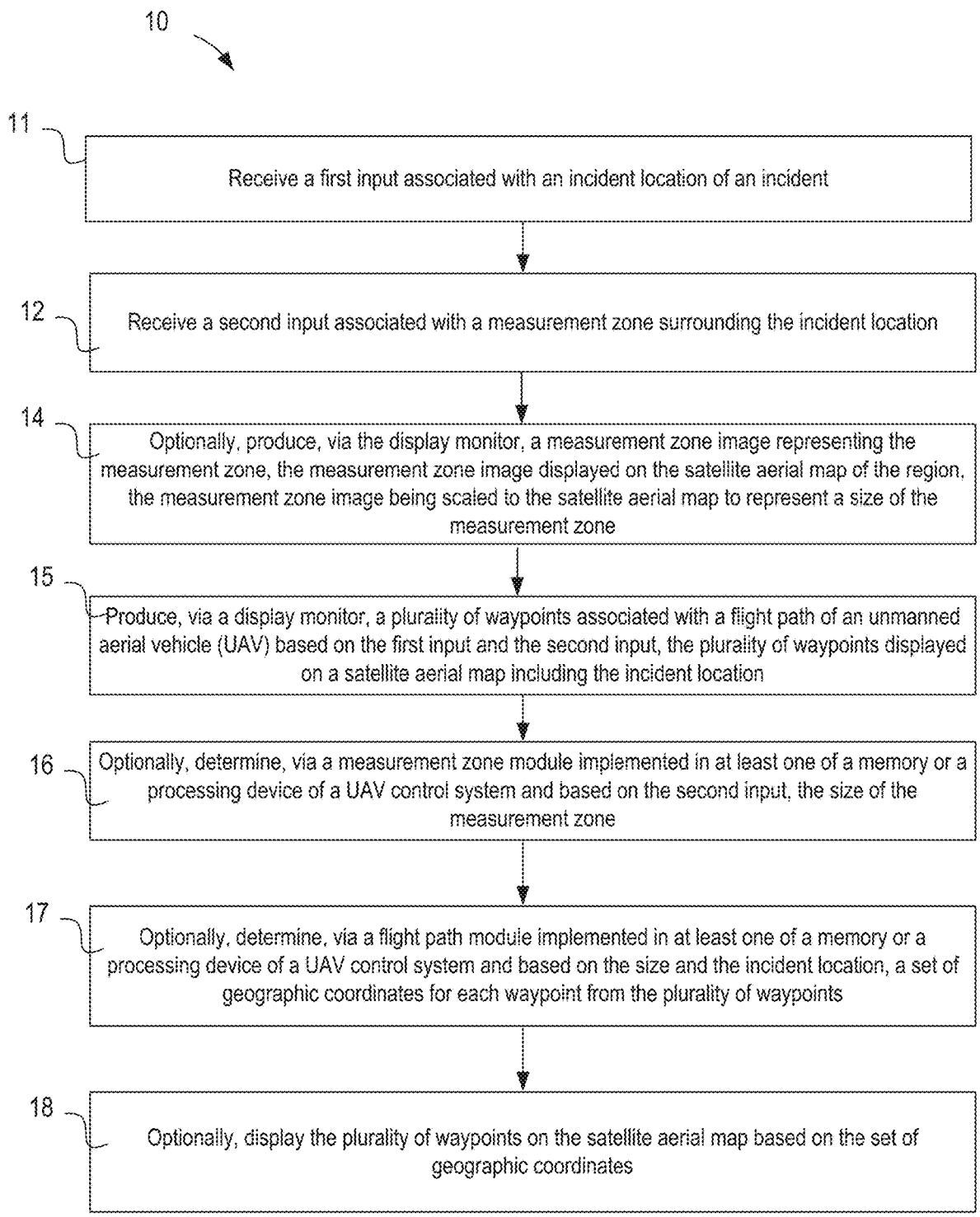
FIG. 2 is a flow chart of a computer-related method of producing one or more flight path waypoints, according to an embodiment.

In some embodiments, any application modules and/or other portions of the electronic circuit system 110 can be operable to perform any of the methods described herein. For example, FIG. 2 is a flow chart of a method 10 of producing one or more flight path waypoints and/or flight paths, according to an embodiment. The method 10 can be performed by the system 100 described above, or any other system described herein. The method 10 is described in conjunction with the schematic illustrations in FIGS. 3-6, which show images displayed on the display monitor 102. In other embodiments, however, the method 10 can be used to generate any other flight paths, waypoints, or the like. The method includes receiving a first input associated with an incident location of an incident, at 11. The first input (incident location) can be received in any suitable format by the input module 120, as described above. As shown in FIG. 3, the incident location 161 can be shown on the satellite aerial map (or image) 160.

A second input associated with a measurement zone surrounding the incident location is received, at 12. The second input can be any suitable information or set of information, and can be received by the input module 120, as described above. For example, in some embodiments, the second input includes the size of the measurement zone. In other embodiments, the second input includes an identification of the hazardous substance and an amount of the hazardous substance. In some embodiments, the method optionally includes producing, via the display monitor, a measurement zone image representing the measurement zone, at 14. The measurement zone image is displayed on the satellite aerial map of the region and is scaled to the satellite aerial map to represent a size of the measurement zone. For example, referring to FIG. 3, the measurement zone image 162 can represent the actual measurement zone surrounding the incident site 161. The measurement zone can be of any shape, size, and orientation, and can be associated with any type zone specified in emergency response guidelines. For example, although the measurement zone image 162 is shown as being a triangle, in other embodiments, the measurement zone image 162 can be circle about the incident site 161 (e.g., an isolation zone), an arc-shaped zone including the incident site 161 (e.g., a protective action zone), or any other suitable zone. In some embodiments, the measurement zone image 162 can be a colored section having an opacity so that the underlying map 160 can be viewed through the measurement zone image 162. In some embodiments, the method can optionally include adjusting the opacity level of the measurement zone image 162.

The method further includes producing, via a display monitor, a set of waypoints associated with a flight path of an unmanned aerial vehicle (UAV) based on the first input and the second input, at 15. Specifically, the set of waypoints is displayed on a satellite aerial map of a region including the incident location. For example, referring to FIG. 4, the method can include producing waypoints 171 on the aerial map 160 that includes the incident location 161. Although FIG. 4 shows four waypoints (identified as points 1-4), in other embodiments, any number of waypoints can be produced. The waypoints can be determined and produced by any application module and by any method as described herein. For example, in some embodiments, the set of waypoints can be specific to a desired hazard sampling mission to be completed by the UAV. For example, the method can further include determining a set of flight segments connecting the waypoints to define a specific flight path that is optimized for data collection. The waypoints and/or the flight segments can be determined so that the flight path traverses desired portions of the measurement zone and/or the incident site. For example, in some embodiments, the waypoints and/or the flight segments can be determined so that at least one flight segment intersects the incident location and another flight segment is tangent to (and/or traverses along) a boundary of the measurement zone. One example of such a method is the production of a flight path for an isolation zone survey, as described below with reference to FIGS. 14 and 16. In other embodiments, the waypoints and/or the flight segments can be determined so that at least one flight segment is aligned with a wind direction. For example, as shown in FIG. 6, the central flight segment 172 is aligned with (or substantially parallel to) the wind direction, as indicated by the arrow AA. As shown, the flight path 170 is rotated (as shown by the arrow BB in FIG. 6) relative the flight path of FIG. 5 to be oriented or aligned with the wind direction. In yet other embodiments, the waypoints and/or the flight segments can be determined so that at least one flight segment is in an upwind direction and another flight segment is in a downwind direction relative to the incident site.

In some embodiments, the method can optionally include determining the size of the measurement zone based on the input received, at 16. In this manner, the method does not rely on an operator to look up and/or enter the size of the measurement zone, thereby improving efficiency and accuracy of the measurement zones and flight paths produced. Specifically, in some embodiments, a measurement zone module (e.g., the module 121) can receive a variety of inputs, as described above, and automatically (i.e., without further human input) determine the measurement zone size.

In some embodiments, the method can optionally include determining a set of geographic coordinates for each waypoint and/or for the flight path, at 17. By producing geographic coordinates (e.g., longitude and latitude) or other coordinates for spatially locating the waypoints and/or flight path, the waypoints and/or flight path can be displayed along with (i.e., superimposed or overlaid onto) the satellite aerial image of the incident site, at 18.

Figure 7:
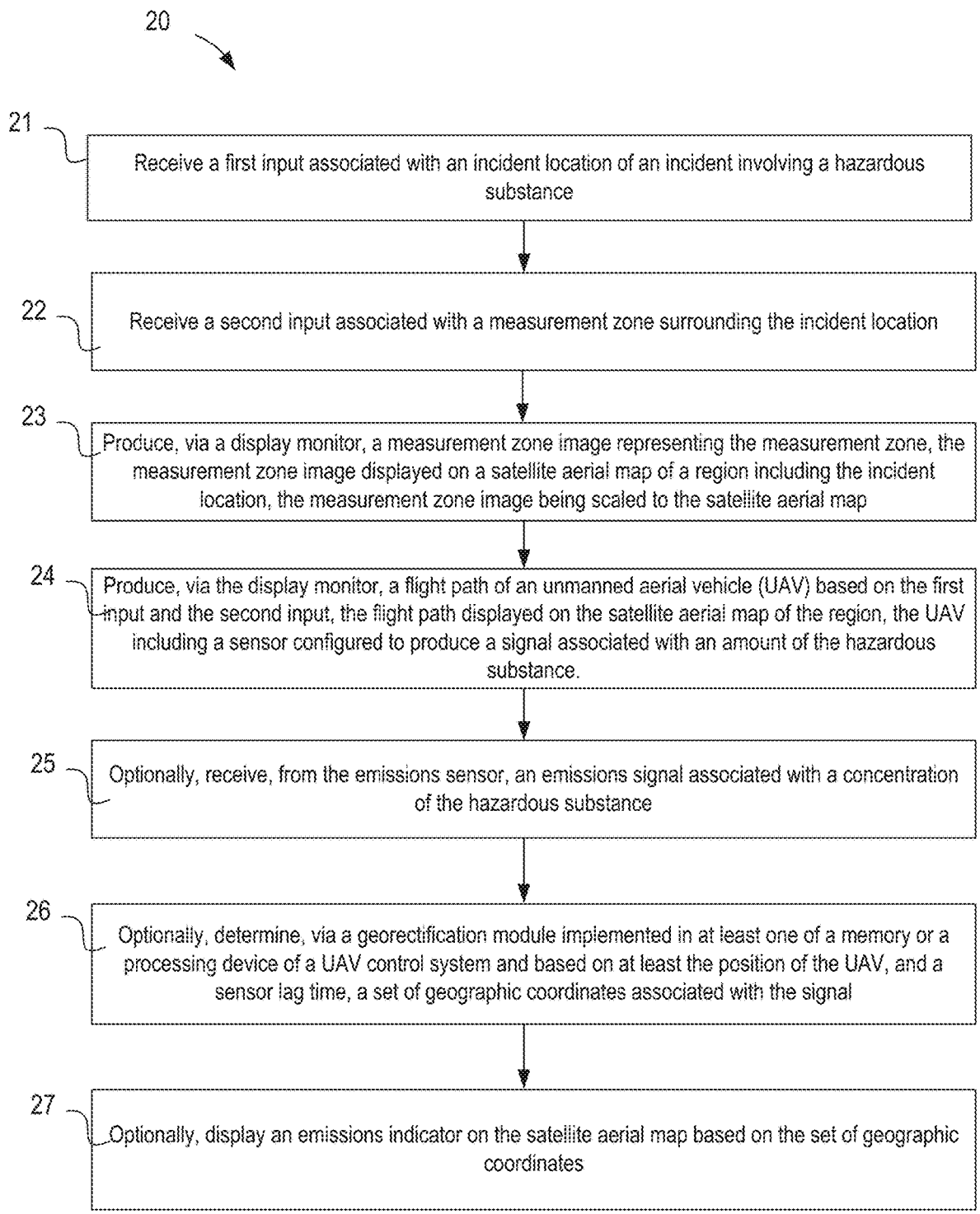
FIG. 7 is a flow chart of a computer-related method of producing a flight path, according to an embodiment.

As another example, FIG. 7 is a flow chart of a method 20 of producing one or more flight path waypoints and/or flight paths, according to an embodiment. The method 20 can be performed by the system 100 described above, or any other system described herein. Moreover, certain operations of the method 20 are similar to that described above with reference to the method 10 and are therefore not described in great detail. The method includes receiving a first input associated with an incident location of an incident involving a hazardous substance, at 21. The first input (e.g., incident location) can be received in any suitable format by the input module 120, as described above. A second input associated with a measurement zone including the incident location is received, at 22. The second input can be any suitable information or set of information, and can be received by the input module 120, as described above. The method further includes producing, via a display monitor, a measurement zone image representing the measurement zone, at 23. The measurement zone image is displayed on a satellite aerial map of the region and is scaled to the satellite aerial map to represent a size of the measurement zone. As described herein, the measurement zone can be of any shape, size, and orientation, and can be associated with any type zone specified in emergency response guidelines. The method further includes producing, via a display monitor, a flight path of an unmanned aerial vehicle (UAV) based on the first input and the second input, at 24. Specifically, the flight path is displayed on a satellite aerial map of a region including the incident location.

As described herein, the UAV can include one or more emissions sensors that produce signals associated with an amount (or concentration) of the hazardous substance when the UAV traverses the flight path. In some embodiments, the system 100 (or any of the systems described herein) can, in addition to producing the desired flight plan, also display the collected data on the display monitor 102. This allows emergency responders to quickly assess the hazard and prepare or modify response plans. For example, if the collected data indicates that the initial size of the isolation zone (as input by the user) was conservative (i.e., larger than needed), then the hazardous information display (i.e., the emissions indicators) can alert the response team to adjust the response plans.

Returning to FIG. 7, in some embodiments, the method 20 can optionally include receiving, from the emissions sensor, an emissions signal associated with a concentration of the hazardous substance, at 25. A set of geographic coordinates associated with the emissions signal is then determined, at 26. The emissions geographic coordinates can be produced, for example, by a georectification module that ensures the spatial accuracy of the emissions signal with respect to the position signal received. The georectification module, and associated methods, is described below with respect to FIGS. 8-10. In some embodiments, the emissions geographic coordinates can be based on at least the position of the UAV and a sensor response time. In this manner, the emissions data can be displayed on the satellite aerial map based on the emissions geographic coordinates, at 27.

Figure 8:
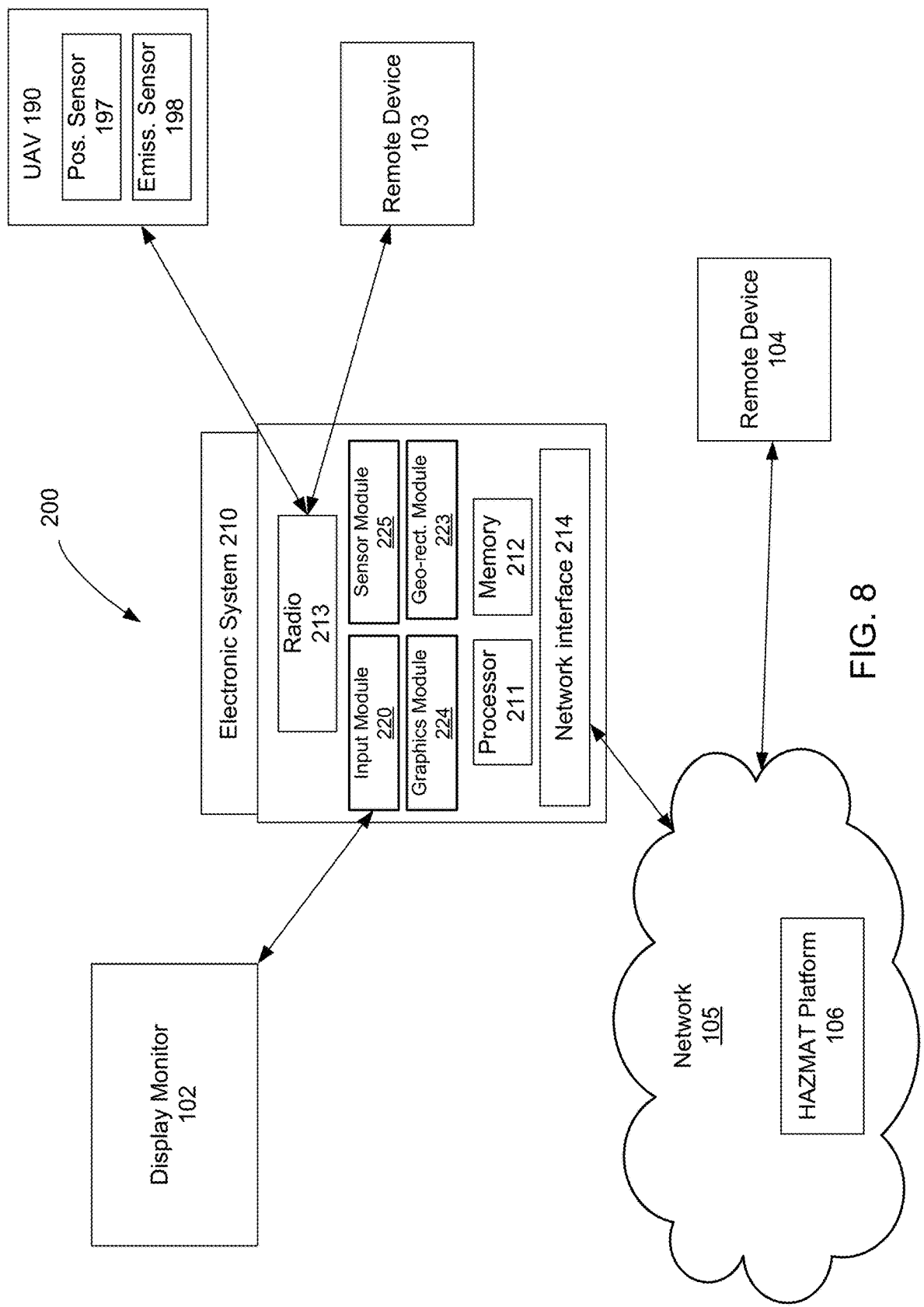
FIG. 8 is a schematic illustration of an emissions display system for an unmanned aerial vehicle (UAV) according to an embodiment.

Referring now to FIG. 8, in some embodiments a display system 200 can be used to display hazardous information (i.e., emissions data) collected by the UAV on a satellite aerial map. As described herein, such systems can include a georectification module 223 that ensures the spatial accuracy of the emissions data displayed on the map. Specifically, the georectification module 223 and methods described herein can accommodate various time delays (referred to herein as sensor lag or response time) that result when taking emissions measurements. Sensor lag can result from a number of different measurement phenomena, including the time required for a desired volume of gas to be sampled by the emissions sensor 197, the time required for the volume of gas to be processed (e.g., the time for the sampling technique to be completed), and the time required for processing of and/or producing of the electronic signal. Thus, the sensor response time can be different for the different sensors included on the UAV 190. Moreover, the sensor response time associated with the emissions sensors 197 (e.g., the CBR sensors) can be different than any response time associated with the position signal(s) produced by the position sensor 197. Thus, simply producing a display of the emissions data "as received" may result in a display that is not geospatially accurate. As shown schematically in FIG. 10, the UAV 190 continuously collects emissions data when it travels along a flight path 370. Thus, when UAV approaches point 2 along the flight path 370, the position signal transmitted to the electronic circuit system 210 may accurately represent (within a negligible time lag) that the position of the UAV is at point 2. The emissions signal(s) transmitted to the electronic circuit system 210, however, may more accurately represent the emissions levels at a prior point (e.g., point 1) along the flight path 370, due to the sensor response time (represented as $\Delta t$ in FIG. 10). Moreover, because the sensor response time for each sensor on the UAV 190 can be different, the emissions data may not be rectified using a single offset value. Further, because the distance traveled during the sensor response time $\Delta t$ is a function of the UAV airspeed, the georectification of the data must account for the speed. As described below, the system 200 (and the methods associated therewith) provides for georectification of the sampled data.

FIG. 8 is a schematic illustration of a UAV display system 200 (also referred to herein simply as "the system 200") according to an embodiment. The system 200 is designed to interface with the UAV 190, which includes one or more position sensors 197 and one or more emissions sensors 198, as described above with reference to the system 100. As shown, the system 200 includes the display monitor 102 and an electronic circuit system 210. The system 200 can optionally be operatively coupled to a first remote device 103 and a second remote device 104, as described above with reference to the system 100. Additionally, the second remote device 104 can be coupled to the electronic circuit system 210 via a network 105. The UAV display system 200 is configured to perform any of the methods described herein, including receiving and graphing emissions data, filtering the data, and processing the data for more efficient viewing and storage.

The electronic circuit system 210 can be any suitable computing device or set of devices to perform the functions described herein. In some embodiments, the electronic circuit system 210 can be a specialized UAV control computer, or the like. As shown, the electronic circuit system 210 includes a processor 211, a memory 212, a radio 213, and a network interface 214. These components of the electronic circuit system 210 are the same as the corresponding components described above for the electronic circuit system 110 and are therefore not described in detail below. The electronic circuit system 210 also includes an input module 220, a georectification module 223, a sensor module 225, and a graphics module 224. Although shown as including each of the input module 220, the georectification module 223, the sensor module 225, and the graphics module 224, in other embodiments an electronic circuit system need not include all (or any) of these modules, and can include any other modules described herein, such as a flight path module, (e.g., the flight path module 122 described with respect to FIG. 1). Moreover, although shown as including a series of components within one device, in other embodiments, the electronic circuit system 210 can include certain portions in one device (and at one location) and other portions in another device (and at another location). For example, in some embodiments, the electronic circuit system 210 can include the radio 213 in one device near the incident location and one or more of the application modules (e.g. the georectification module 223) in a second, separate device that is remotely located.

The input module 220 can be a hardware and/or software module (stored in memory 212 and/or executed in the processor 211). As described in more detail herein, the input module 220 is configured to receive one or more inputs related to a hazardous incident. The input module 220 can receive the inputs in any suitable manner. For example, in some embodiments, the input module 220 can receive one or more inputs in response to an input prompt displayed on the display monitor 202. For example, in some embodiments inputs related to the sensor setup, incident site, or the like can be entered in response to prompts presented via a HAZMAT input menu (see e.g., the HAZMAT input window 440 shown and described below with reference to FIG. 11). For example, as described below the input module 220 can receive one or more inputs in response to a sensor calibration prompt 484A (FIG. 11) or a sensor settings prompt 484B (FIG. 12). In other embodiments, the input module 220 can receive one or more inputs from the remote device 103 and/or the remote device 104. For example, in some embodiments, inputs related to local wind direction, temperature, and time of day can be received directly from either remote device. In this manner, the inputs can be received with limited manual input, thereby improving accuracy and efficiency of receiving the inputs.

In other embodiments, the input module 220 can receive one or more inputs regarding the desired spatial resolution for each sensor. Referring again to FIG. 10, when the average speed of the UAV increases, the distance traveled by the UAV during the sensor response time increases. Thus, if a high spatial resolution is required, the UAV should be operated at a slow airspeed. Conversely, if the total length of the flight path 370 is such that the UAV must operate at a faster airspeed to complete the mission, then the spatial resolution of the emissions data may be reduced. Similarly stated, the highest resolution data will occur at the slowest speeds. In some embodiments, the emissions data is displayed as one or more emissions indicators on the satellite aerial map/image (see e.g., the emissions indicators 382A and 382B in FIG. 10). Each of the emissions indicators occupies an area on the display that is scaled to correspond to a physical size within the measurement zone or flight path. For example, in some embodiments, each emission indicator (or "square") can represent an actual area of 10 square feet. In some embodiments, the input module 220 can receive an input to change the spatial resolution of the emissions indicators. For example, in situations where the UAV 190 will be traveling at higher airspeeds the user may need to change the spatial calibration of the emissions indicators to represent a larger area (e.g., 20 square feet). In other words, the resolution will be decreased. Table 1 below provides a correlation between the emissions indicator size (actual area) vs. UAV flight speed for some embodiments.

TABLE 1

| Average Speed (mph) | Emissions Indicator Size (sq. ft.) |
|---|---|
| <1 | 10 |
| 1-3 | 20 |
| 4-5 | 30 |
| 6-7 | 50 |
| 8-14 | 60 |
| 15-18 | 100 |
| 19-20 | 150 |

The sensor module 225 can be a hardware and/or software module (stored in memory 212 and/or executed in the processor 211). The sensor module 225 is configured to receive an emissions signal from the emissions sensor(s) 198 and a position signal from the position sensor(s) 197. For example, in some embodiments, the sensor module 225 is operatively coupled to the radio 213, and can include the circuit components (electronic filters, converters, and the like) to receive and process the signals.

The georectification module 223 can be a hardware and/or software module (stored in memory 212 and/or executed in the processor 211). As described in more detail herein, the georectification module 223 is configured to generate a set of geographic coordinates associated with each emissions signal to ensure that the emissions data can be displayed accurately via the display monitor 102. Similarly stated, the georectification module 223 is configured to generate a set of geographic coordinates for each emissions signal received based on at least the position signal and a sensor response time for the sensor. For example, in some embodiments, the sensor signal and the position signal are received by the sensor module 225 as a data packet. Each data packet is a grouping of signals that correspond to a particular time, and each data packet can include, for example, a signal for each sensor, a time stamp, and one or more position signals (e.g., an altitude signal, a GPS location, and/or an airspeed reading). In such embodiments, the georectification module 223 is configured to generate a set of geographic coordinates for each data packet and can accommodate different sensor response times for each of the sensors for which sensor signals are included in the data packet. In other embodiments, the sensor response time can be substantially the same for each of the sensors for which sensor signals are included in the data packet. As described below, the graphics module 224 can accurately display the emissions data.

The graphics module 224 can be a hardware and/or software module (stored in memory 212 and/or executed in the processor 211). The graphics module 224 is configured to display a set of images on the display monitor 202 to facilitate the emissions data sampling by the UAV 190, evaluations of the received emissions data, and the like. Specifically, the graphics module 224 is configured to display a satellite aerial map of a region including the incident location. For example, referring to FIGS. 13 and 14, the graphics module can display a satellite aerial map 460 of a region that includes the incident location 461. The graphics module 224 is also configured to display a measurement zone image representing the measurement zone, a set of waypoints, and/or a flight path, as described herein. For example, FIGS. 14,15, 18, and 19 are images showing an isolation zone image 463 and/or a protective action zone image 464 displayed on a satellite aerial map 460.

Additionally, the graphics module 224 is configured to display one or more emissions indicators on the satellite aerial map to graphically depict the measured emissions. For example, referring to FIGS. 23 and 26, the graphics module 224 can display a series of emissions indicators 482 (which appear as squares or pixels) based on the geographic coordinates produced by the georectification module. In this manner, the emissions indicators can be scaled to represent a region on the map corresponding to the concentration (or amount) of the hazardous material (or substance) and can be geospatially accurate. In some embodiments, the graphics module 224 can adjust the size (or area) of the emissions indicators to correspond to the desired spatial resolution, as described above. In some embodiments, the graphics module 224 can select a color associated with the concentration (amount) of the hazardous material (or substance) and produce that color within the emissions indicator. For example, in areas of unsafe hazardous material (or substance) concentration, the emissions indicator(s) can be red, whereas in areas where the concentration of hazardous material (or substance) is below a safe threshold, the emissions indicators can be green.

Further, in some embodiments, the graphics module 224 is configured to adjust the characteristics of the emissions indicators displayed. For example, in some embodiments the emissions indicators can be displayed with an opacity such that portions of the underlying satellite image can be viewed.

Figure 9:
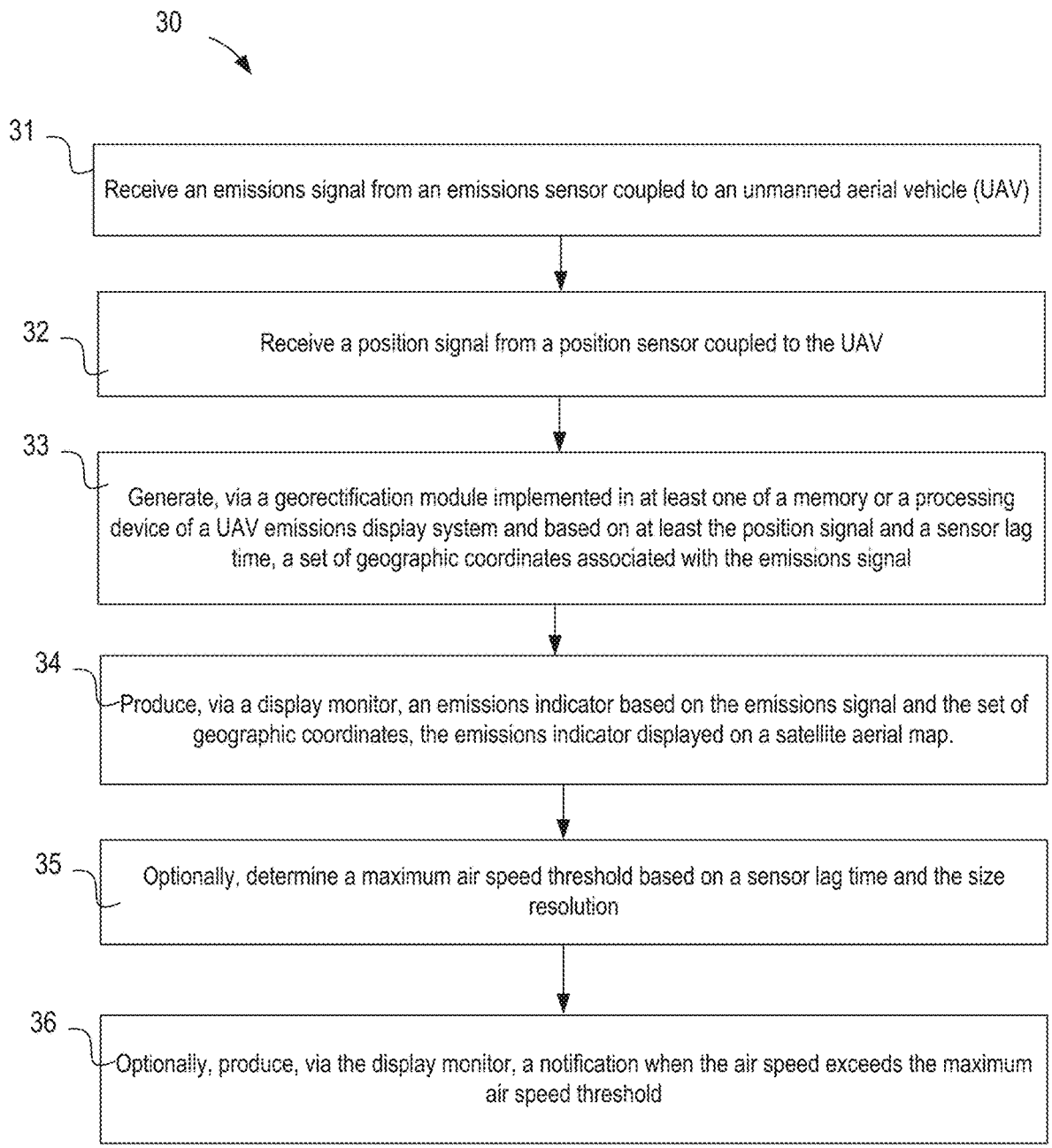
FIG. 9 is a flow chart of a computer-related method of displaying emissions information collected by a UAV, according to an embodiment.
Figure 10:
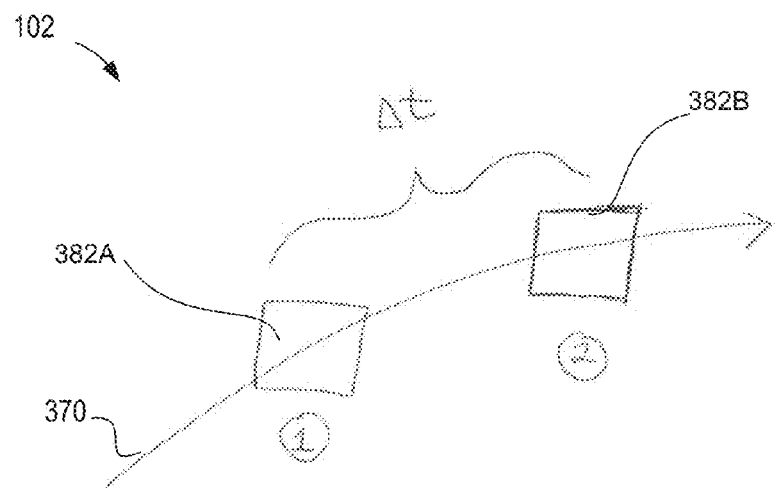
FIG. 10 is a schematic illustration of a portion of a satellite aerial map including an emissions indicator produced by the display system shown in FIG. 8 or according to the method shown in FIG. 9.

In some embodiments, any application modules and/or other portions of the electronic circuit system 210 can be operable to perform any of the methods described herein. For example, FIG. 9 is a flow chart of a method 30 of producing one or more emissions indicators on a satellite image map, according to an embodiment. The method 30 can be performed by the system 200 described above, or any other system described herein. The method includes receiving an emissions signal from an emissions sensor coupled to an unmanned aerial vehicle (UAV), at 31. The method further includes receiving a position signal from a position sensor coupled to the UAV, at 32. As described above, the emissions signal and the position signal can be included within a data packet. Moreover, the emissions signal and position signal can be a set of signals from one or more emissions sensors and one or more position sensors, as described above.

A set of geographic coordinates associated with the emissions signal is then generated, at 33. The geographic coordinates can be generated by the georectification module 223 and in the manner as described above. For example, the geographic coordinates can be generated based on at least the position signal and a sensor response time. An emissions indicator is then displayed on a satellite aerial map, at 34. The emissions indicator can be displayed via a graphics module 224 and in the manner described above.

As described above, the resolution of the emission indicator is related to the airspeed of the UAV. Accordingly, in some embodiments, the method optionally includes determining a maximum air speed threshold based on the sensor response time and the selected size resolution, at 35. For example, referring to Table 1 above, if the selected size resolution is 20 square feet, the maximum speed threshold is 3 miles per hour. The method can further optionally include producing, via the display monitor, a notification when the air speed of the UAV exceeds the maximum air speed threshold, at 36. In other embodiments, the method can optionally include sending a control signal to the UAV to limit the speed (i.e., to preserve the desired data resolution).

Figure 11:
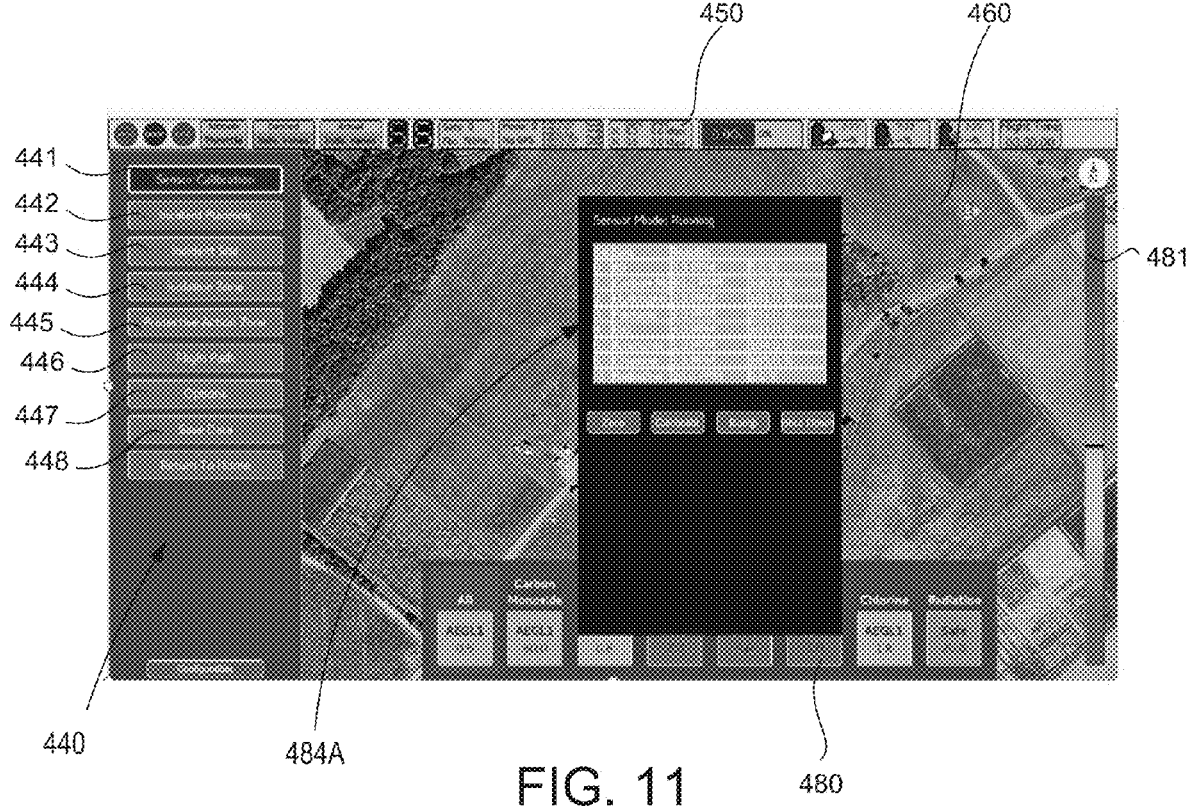
FIG. 11 is an image on a display monitor showing a graphical output, including a sensor calibration window, produced by a control system according to an embodiment.
Figure 12:
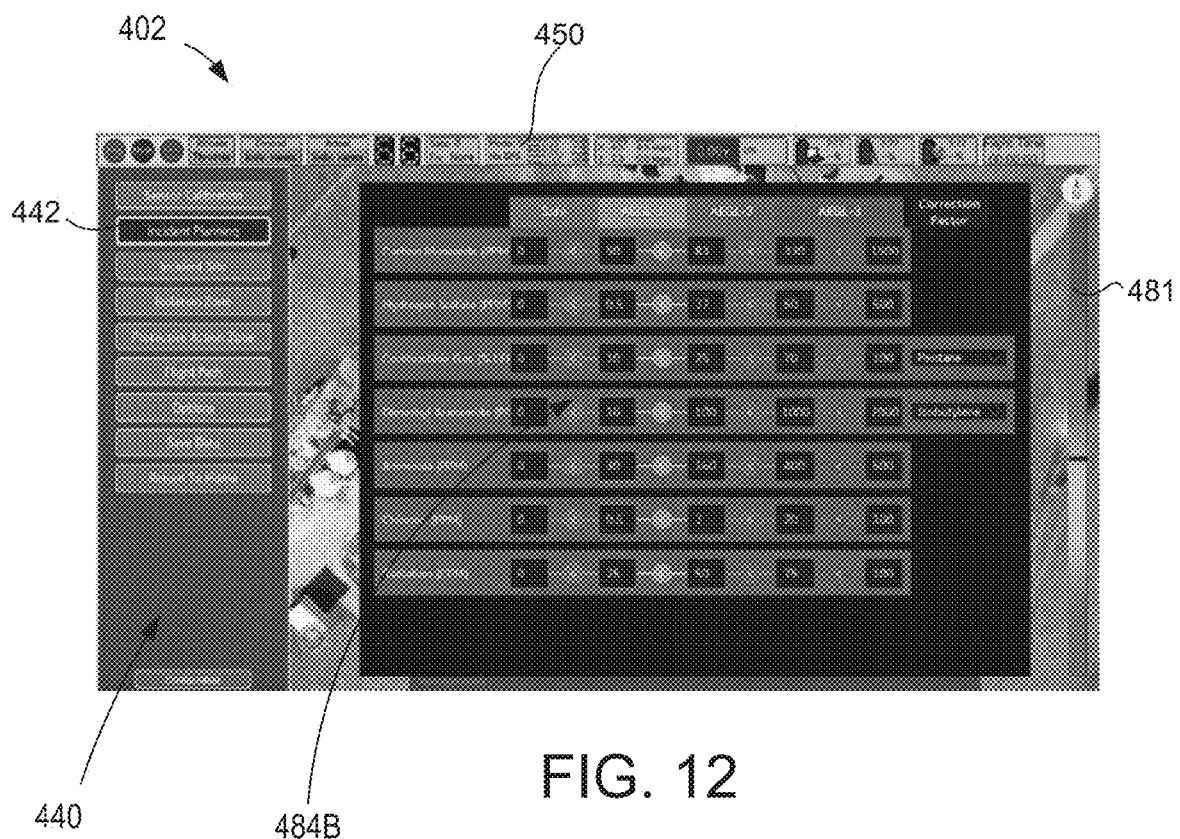
FIG. 12 is an image on a display monitor showing a graphical output, including a sensor setup window, produced by a control system according to an embodiment.
Figure 14:
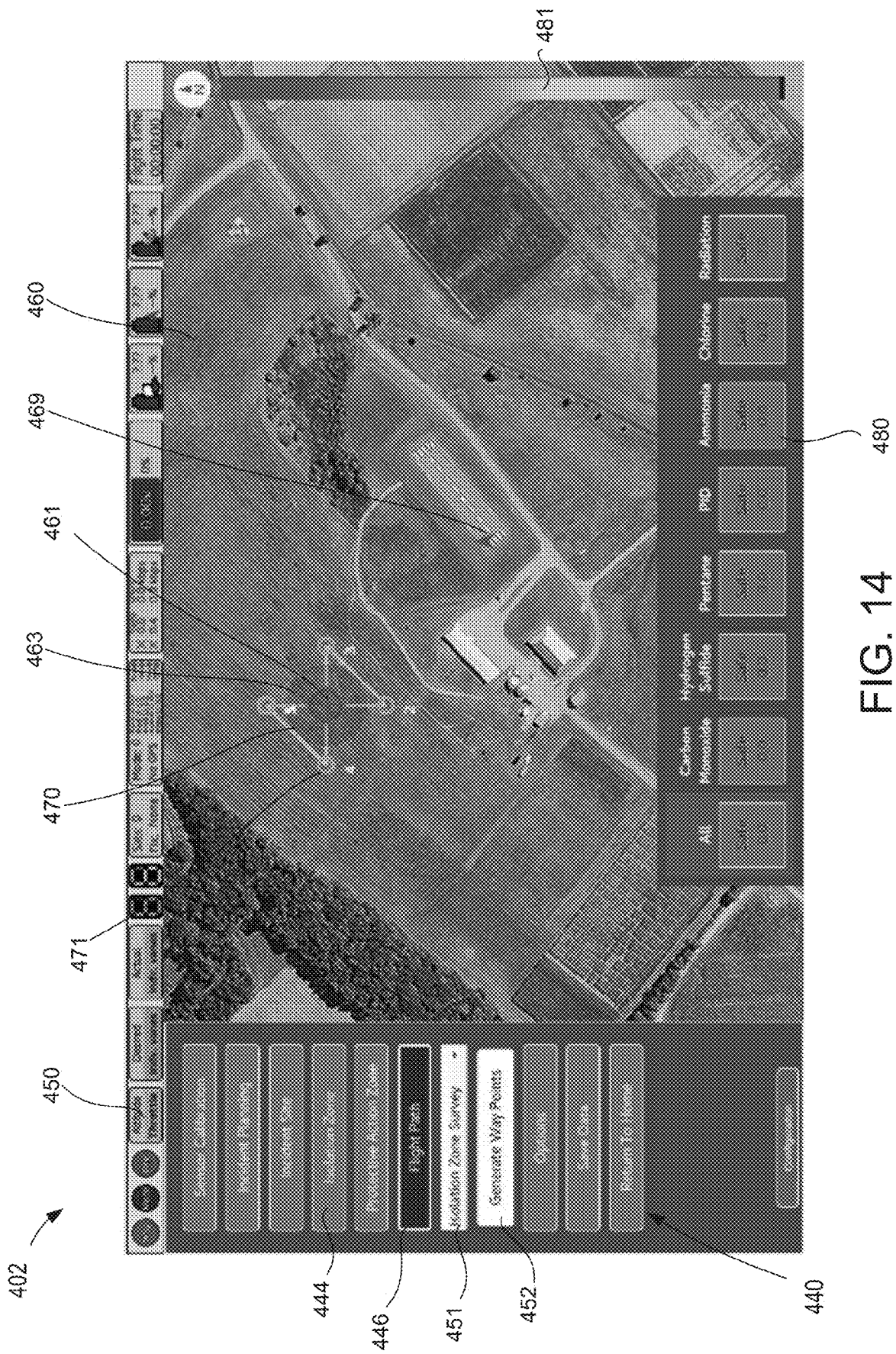
FIGS. 14 and 15 are images on a display monitor showing measurement zones displayed on a satellite aerial map or image, produced by a control system according to an embodiment.
Figure 15:
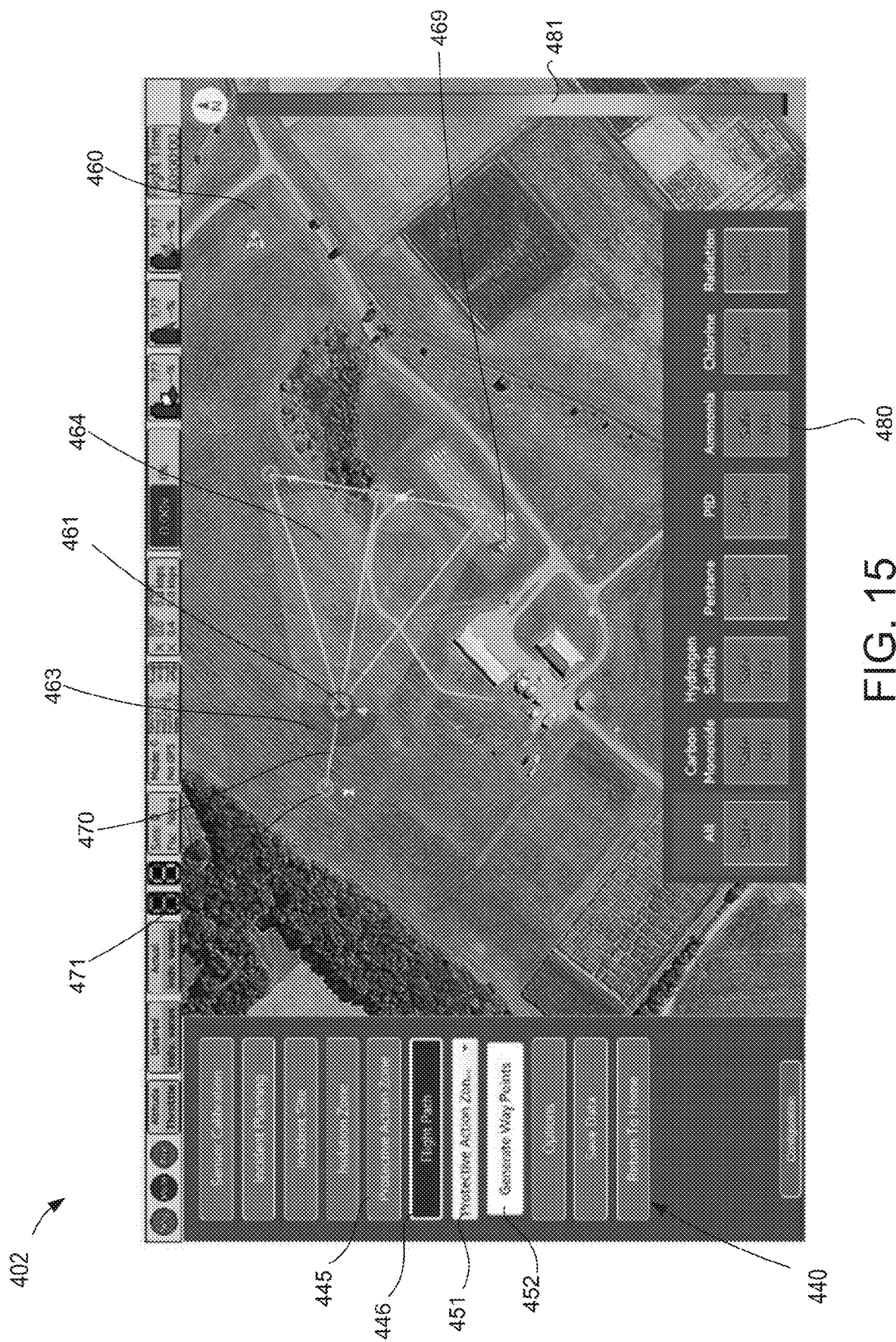
Figure 16:
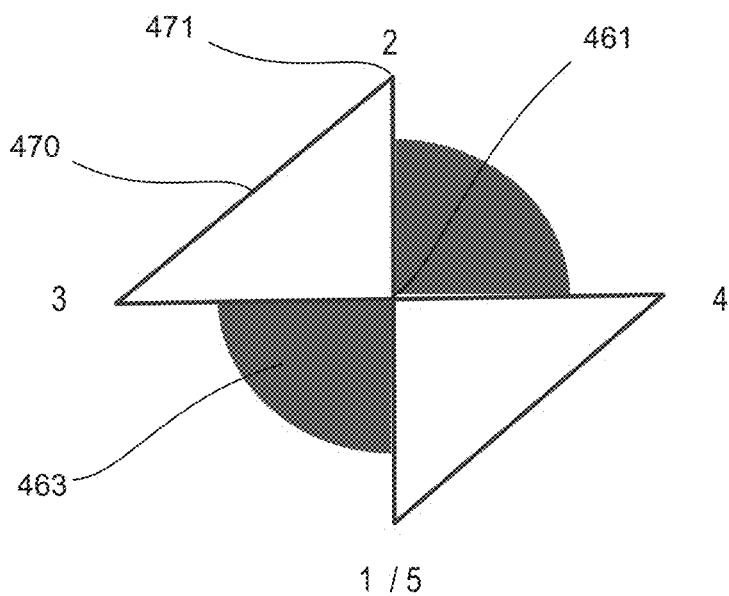
FIG. 16 is a schematic illustration of a flight path within a measurement zone produced by a control system or methods according to an embodiment.
Figure 17:
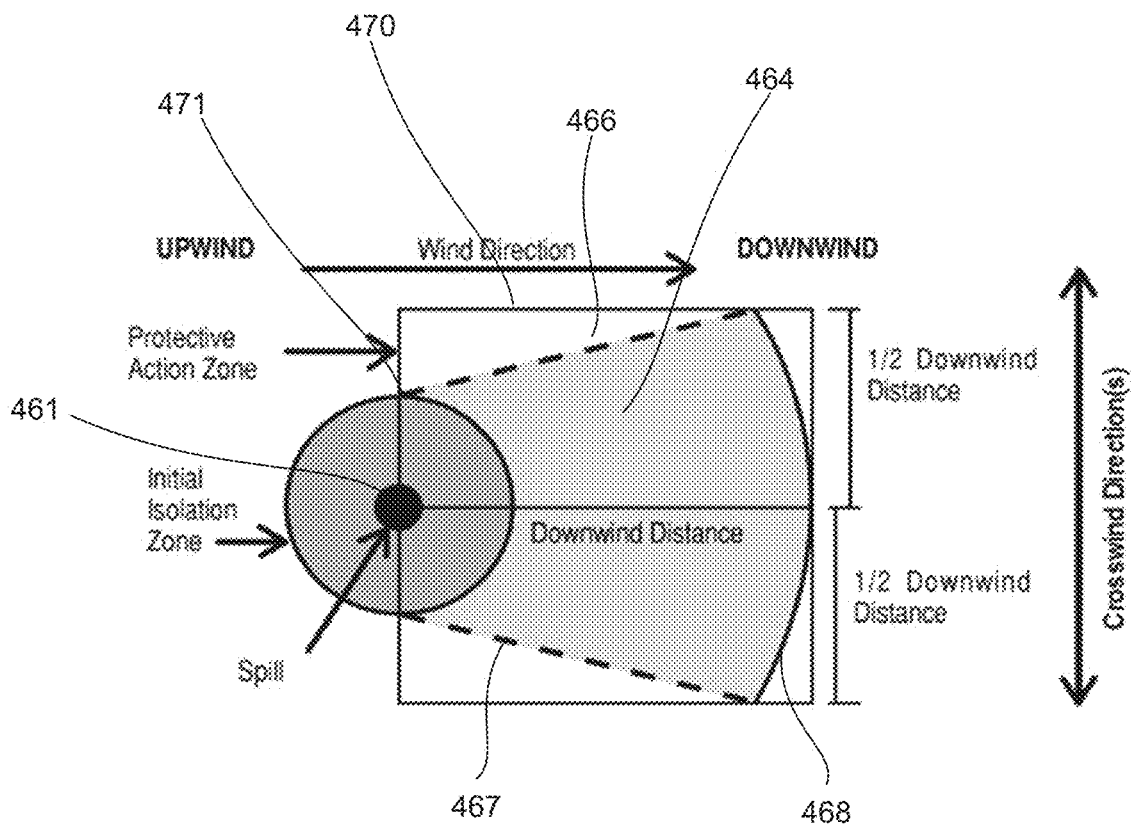
FIG. 17 is a schematic illustration of a protective action zone used in conjunction with the systems and methods described herein.
Figure 21:
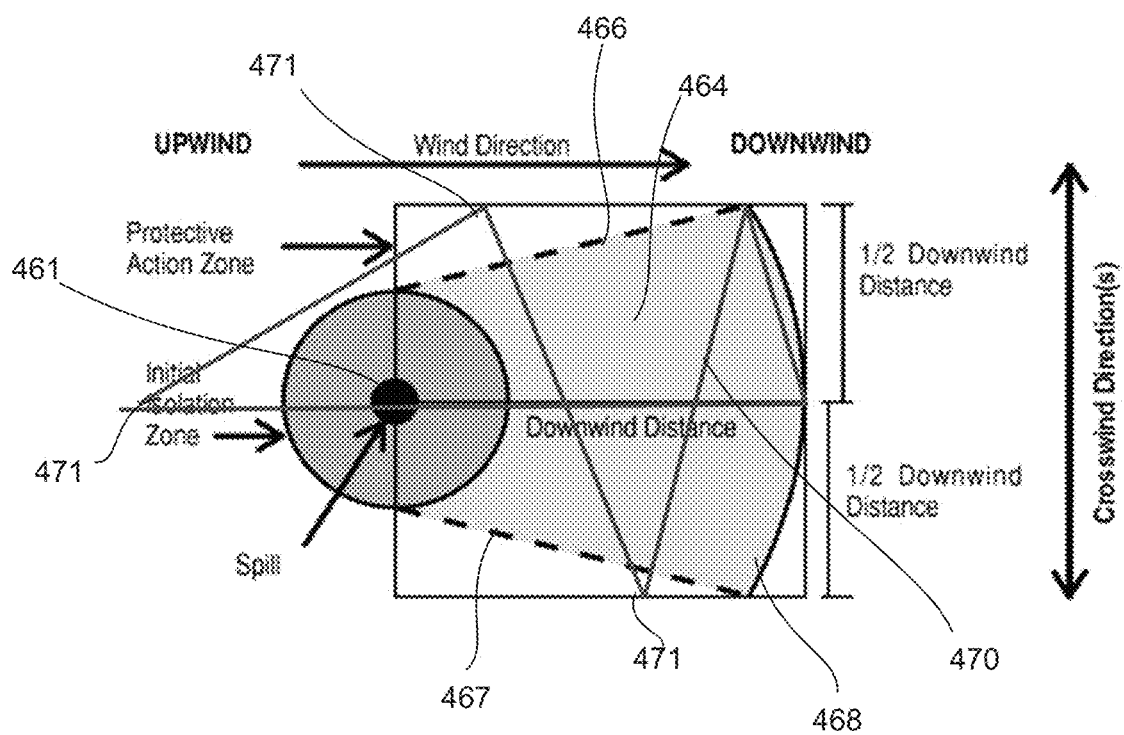

FIGS. 11-15, 18-20, and 23 are various images produced on a display monitor 402 and FIGS. 16, 17, 21, and 21 are various schematic illustrations that collectively demonstrate one or more methods according to various embodiments. The display monitor 402 can be similar to the display monitor 102 described herein and can be included within (and the images can be produced by) any of the systems described herein, such as the system 100 or the system 200. FIG. 11 shows the general display produced by the system 100 or the system 200. The display includes an input menu 440 (also referred to as the HAZMAT input window 440) that, as described above, can be used via the input module 120 or the input module 220 to input information regarding the desired mission into the system. The input menu 440 includes a sensor calibration prompt 441, an incident planning prompt 442, an incident site input prompt 443, an isolation zone input prompt 444, a protective action zone input prompt 445 (the isolation zone input and the protective action zone input can generally be referred to as measurement zone input prompts), a flight path prompt 446, an options prompt 447, and a data save prompt 448. Each of these prompts, and the associated methods are described in more detail below.

The top of the display includes a UAV control ribbon 450 upon which information about the flight of the UAV can be displayed. The right edge of the display includes a hazard level scale 481. As described below, the hazard level scale 481 includes a scale of colors that represents a hazard level associated with a range of concentration (or amount) of a measured hazardous material (or substance). The colored scale corresponds to an exposure level based on safety standards (e.g., the Acute Exposure Guideline Level standards) and thus provides an efficient mechanism for evaluating the emissions indicators plotted (see e.g., FIGS. 23A and 23B) so that the user can quickly assess areas of safety within the measured zones. For example, a red colored emissions indicator (or series of emissions indicators) can indicate a spatial region with unsafe levels of one or more materials, while a green colored emissions indicator (or series of emissions indicators) can indicate a spatial region with safe levels of all measured materials. Moreover, as described below, the hazard level scale 481 is a single scale that standardizes the various different exposure level effects for all of the various materials for which measurements are taken to one color scale. The bottom portion of the display includes a sensor visualization ribbon 480.

Referring to FIG. 11, in some embodiments, the system can include a calibration input window 484A in response to selecting the sensor calibration prompt 441. The sensors can be calibrated using any suitable method for calibrating each type of sensor included on the UAV. For example, some sensor can be calibration using a calibration cup and gas cylinder that contains the gas standard. A cup is placed over the sensors, and the user follows the manufacturer's instructions for connecting the calibration gas cylinder and initiating the gas flow. Once the gas is flowing, calibration is initiated for each sensor by and pressing the "Calibrate" button. This will begin the sensor's internal, automatic calibration routine.

Referring to FIG. 12, a sensor settings window 484B is provided in response to selecting the incident planning prompt 442. The sensor settings window 484B allows the user to review, select and/or edit information for the sensors that are coupled to the UAV. Specifically, the sensor settings window 484B shows the threshold values expressed as parts per million (PPM) for hazardous gasses, lower explosive limit (% LEL) for explosive gasses, counts per minute (CPM) for radiation readings, or Percent Volume (% VOL) for Oxygen. Each hazard threshold value and color intensity has been calibrated with the corresponding Acute Exposure Guideline Levels (AEGL), expressed as a concentration. As described above, this enables comparability of the effects of each hazard using the single color scale 481. Specifically, the colors map to the various thresholds ranging from SAFE (green) to AEGL-3 (red). These threshold (i.e., AEGL) values are pre-populated for the sensors, but can be adjusted by the user if different exposure standards or action levels apply to the responders and/or the public. The threshold values are used to determine the colors for the values on the sensor visualization ribbon 480, hazard level scale 481, sensor reading indicators (i.e., the emissions indicators) 482, and map overlay on the sensor visualization window.

Figure 13:
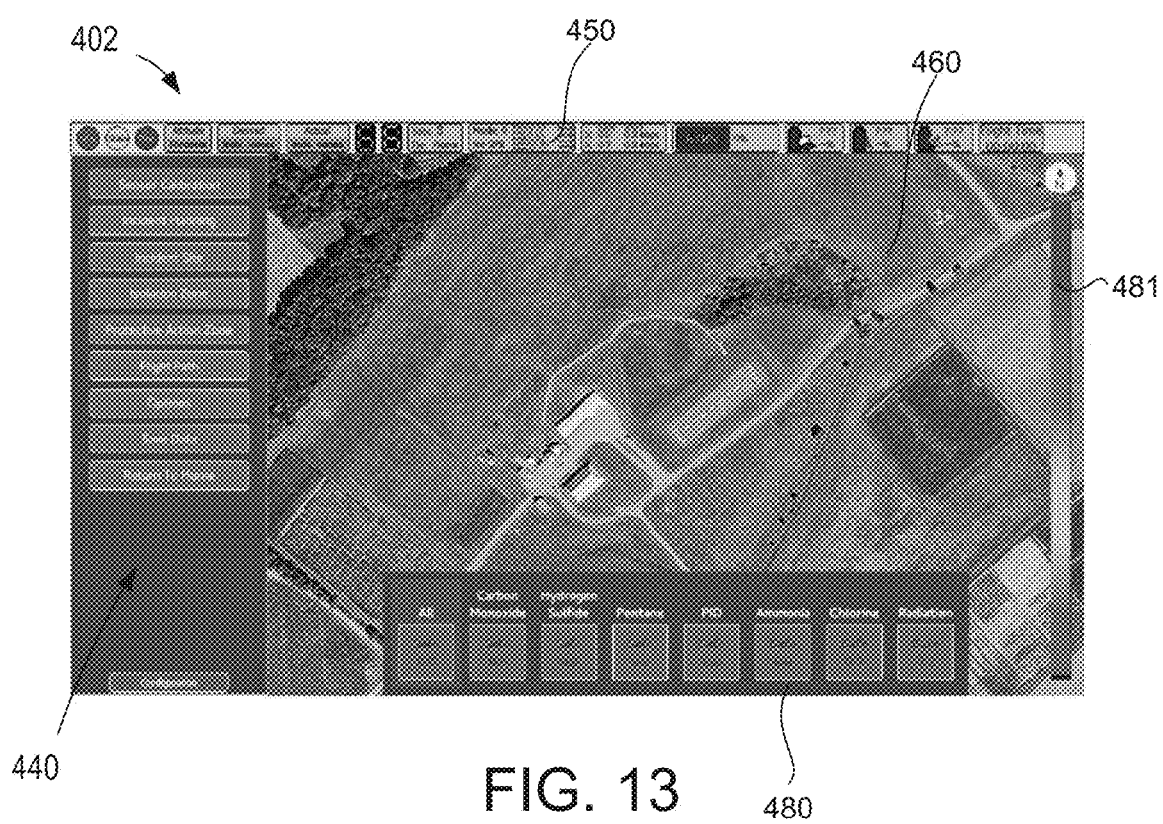
FIG. 13 is an image on a display monitor showing a graphical output, including a satellite aerial map or image, produced by a control system according to an embodiment.

FIG. 13 more clearly shows the satellite aerial map 460 and the sensor visualization ribbon 480. The sensor visualization ribbon 480 is a row of icons including one for each sensor on the vehicle. The color of each icon indicates the hazard intensity for that sensor, categorized as safe, warning, hazardous and dangerous. The hazard level scale 481 shows the full range of readings and indicates the worst case from amongst all the sensors. In this manner, a user can quickly understand if any of the sensors is above a certain threshold. Alternatively, if the user selects a single sensor from the sensor visualization ribbon 480, the emissions indicators plotted will be for that sensor only.

FIG. 14 is an image on the display monitor 402 showing an isolation zone image 463 displayed on the satellite aerial map or image 460. The image also shows the incident location 461 and the current position of the UAV 469. The image also shows includes four waypoints 471, which are shown as green circles (only one waypoint is identified by a reference sign) and a flight path 470 between the various waypoints. The isolation zone image 463, the waypoints 471, and the flight path 470 can be produced by any of the systems described herein, and according any of the methods described herein. In particular, the isolation zone image 463 can be produced by first selecting the isolation zone prompt 444. In response, the user can select or input an isolation zone size (i.e., radius), or in other embodiments, the system can request data about the hazardous incident and determine the size of the isolation zone, as described herein. In some embodiments, the system can produce a drop-down menu with several common isolation zone sizes from which the user can select. The sizes can correspond to the most common isolation zones identified in the North American Emergency Response Guidebook. Upon completing the selection, the system produces the isolation zone image 463 centered about the incident location 461. As shown, the isolation zone image 463 can be blue (or purple) and can have an opacity to allow the underlying map 460 to be viewed.

FIG. 15 is an image on the display monitor 402 showing both the isolation zone image 463 and a protective action zone image 464 displayed on the satellite aerial map or image 460. The image also shows the incident location 461 and the current position of the UAV 469. The image also shows includes several waypoints 471, which are shown as green circles (only one waypoint is identified with a reference sign) and a flight path 470 between the various waypoints. The protective action zone image 464, the waypoints 471, and the flight path 470 can be produced by any of the systems described herein, and according any of the methods described herein. In particular, the protective action zone image 464 can be produced by first selecting the protective action zone prompt 445. In response, the user can select or input a protective action zone size (i.e., downwind distance), or in other embodiments, the system can request data about the hazardous incident and determine the size of the protective action zone, as described herein. In some embodiments, the system can produce a drop-down menu with several common protective action zone sizes from which the user can select. The sizes can correspond to the most common protective action zones identified in the North American Emergency Response Guidebook. In addition to the downwind distance, the user also inputs the wind direction. In some embodiments, this can be input via a remote device. Upon completing the selection, the system produces the protective action zone image 464. In some embodiments, the user can align the orientation of this zone with the wind direction. As shown, the protective action zone image 464 can be a yellow wedge and can have an opacity to allow the underlying map 460 to be viewed.

Prior to flight, a HAZMAT mission can be defined in accordance with any of the methods described herein. The mission parameters can include a selection of sensors from which emissions signal are desired, time constraints, and the type of survey (or flight path) that is desired. To aid the mission planner and incident commander in decision making, the system and methods include several default flight paths that are pre-designed to meet certain incident objectives. A flight path for the mission can be established by selecting the fight path button 446. In response, the system will produce a drop-down menu 451 listing several pre-designed flight paths. After the desired flight path is selected, the waypoints 471 and the flight path 470 can be generated by selecting the generate waypoints button 452. Several paths are available, including: A) a custom flight path where the user selects all waypoints; B) an isolation zone survey (see FIGS. 14 and 16); C) a protective action zone survey to verify the boundaries of the protective action zone (see FIGS. 15 and 17); D) a downwind hazard survey (see FIGS. 18 and 20); E) an extended downwind hazard survey, which is an extended protective action zone survey (see FIGS. 19 and 21); and F) an isolation zone confirmation survey to verify the safety of responders outside of the IZ (see FIG. 22). Each of these flight paths is optimized around flight operational constraints of the UAV. Such constraints include, for example, the battery life (30 minutes), the airspeed limitations of the aircraft (not to exceed 20 mph), sensor response time, maximum flight distance, operator safety distance and endurance. Additionally, these flight paths account for various Hazmat technical response objectives such as the desire to collect the largest amount of the most relevant data to supporting incident commander decisions (e.g., confirming cold zone, defining hot zone, shelter in place, evacuation and responder safety). Each of the specific paths is disclosed in more detail below.

FIGS. 14 and 16 show details of the isolation zone survey. The purpose of the isolation zone survey is to quickly survey the entire isolation zone to determine the size, shape and extent of the hazards in the isolation zone. As shown, the system produces four waypoints 471, which are identified as waypoint 1/5 (the starting and ending point), 2 (the second point traversed), 3 (the third point traversed), and 4 (the fourth point traversed). The flight path 470 includes a series of flight segments, with the first flight segment extended directly across isolation zone 463 (intersecting the incident site 461). The second flight segment is from the second waypoint to the third waypoint and proceeds to a point just beyond the lateral (crosswind) edge of the zone. The third flight segment is from the third waypoint to the fourth waypoint and proceeds directly across isolation zone 463. The fourth flight segment is from the fourth waypoint to the fifth (i.e., first) waypoint and also extends along the tangent line to the isolation zone. Thus, this flight path 470 allows for collection of data along two flight segments that are tangent to the circular isolation zone 463 (one upwind and one downwind) of the zone.

Collecting data along the isolation zone flight path can assist the first responders to confirm, expand, or reduces the size of the isolation zone (IZ) to protect those outside while safely minimizing the distance between responders and the hazard. This can enable rapid offensive tactics, proximal defensive tactics or non-intervention. The data collected also provides indications of hazard migration (speed and direction) outside of the IZ. The data collected can be used to determine proximal shape of the hazard area to support offensive approach and subsequent tactics. This may enable more optimal use of supplied air and reduce heat stress with more appropriate PPE postures. Finally, respiratory protection (RP) selection must be based on identified hazards, maximum hazard concentration and exposure duration. Data collected may lead to less conservative PPE/RP decisions (full face respirator instead of Self-Contained Breathing Apparatus) enabling longer duration of offensive response in the hazard area.

FIGS. 15 and 17 show details of the protective action zone survey. The purpose of the protective action zone (PAZ) survey is to determine the downwind distance of the hazard and any lateral migration of the hazard outside of the PAZ. It also accomplishes some elements of the isolation zone survey by dissecting the IZ and providing useful data along the complete centerline of the IZ and PAZ. Conducting this survey can result in confirmation of the PAZ distance or adjustments to the PAZ ensuring protection of personnel outside of the PAZ. As shown, the system produces a series of waypoints 471 and flight segments to define the flight path 470. The flight path 470 begins upwind of the isolation zone and then dissects the isolation zone and protective action zone to a point at the downwind edge of the protective action zone. The next waypoint is laterally to one downwind corner of the zone. From there the path proceeds to the incident site 461 in the center of the isolation zone and then to the opposite downwind corner of the zone. The next waypoint is at the center downwind location of the zone and then the path finishes by going back to the starting point upwind of the incident site.

Referring to FIG. 17, the perimeter of the protective action zone 464 includes a first edge 466, a second edge 467, and an arc 468 downwind from the incident location. The arc 468 is centered at the incident location 461 and has an arc radius the corresponds (e.g., is equal to) the downwind distance. The arc length can be any suitable distance, and in some embodiments, is based on regulatory guidelines. For example, as shown in FIG. 17, in some embodiments, the arc length extends laterally by one half the downwind distance. As shown, the arc 468 connects the first edge 466 and the second edge 467 to form the protective action zone 464. The first edge 466 and the second edge 467 can be determined in a manner such that they are tangent to the isolation zone circle. In some embodiments, the flight path module is configured to generate a set of waypoints to include a first waypoint on the first edge 466, a second waypoint on the second edge 467, and a third waypoint on the arc 468. In other embodiments, such as the downwind hazard survey described below with reference to FIG. 18, the flight path module is configured to generate a set of waypoints to include a first waypoint on the arc 468 (see waypoint 2), a second waypoint that is on the first edge 466 (see waypoint 3), a third waypoint that produces a flight segment that crosses the second edge 467 (see waypoint 4), and a fourth waypoint that produces a flight segment that crosses the second edge 467 (see waypoint 5).

The protective action zone survey supports decision making in several ways. This survey identifies downwind hazard areas that require evacuation, shelter in place or no protective action. Collecting data along the flight path will confirm, expand, reduce the size of the PAZ. Collecting data along the flight path will help determine the extent of lateral hazard migration within the PAZ. Collecting data along the flight path will establish a safe upwind approach distance to the hazard. Further the data will indicate rate of changing conditions and hazard migration as the first and last leg of the survey are repeated (beginning and end). This may aid in projecting whether the hazard will migrate farther downwind.

Figure 18:
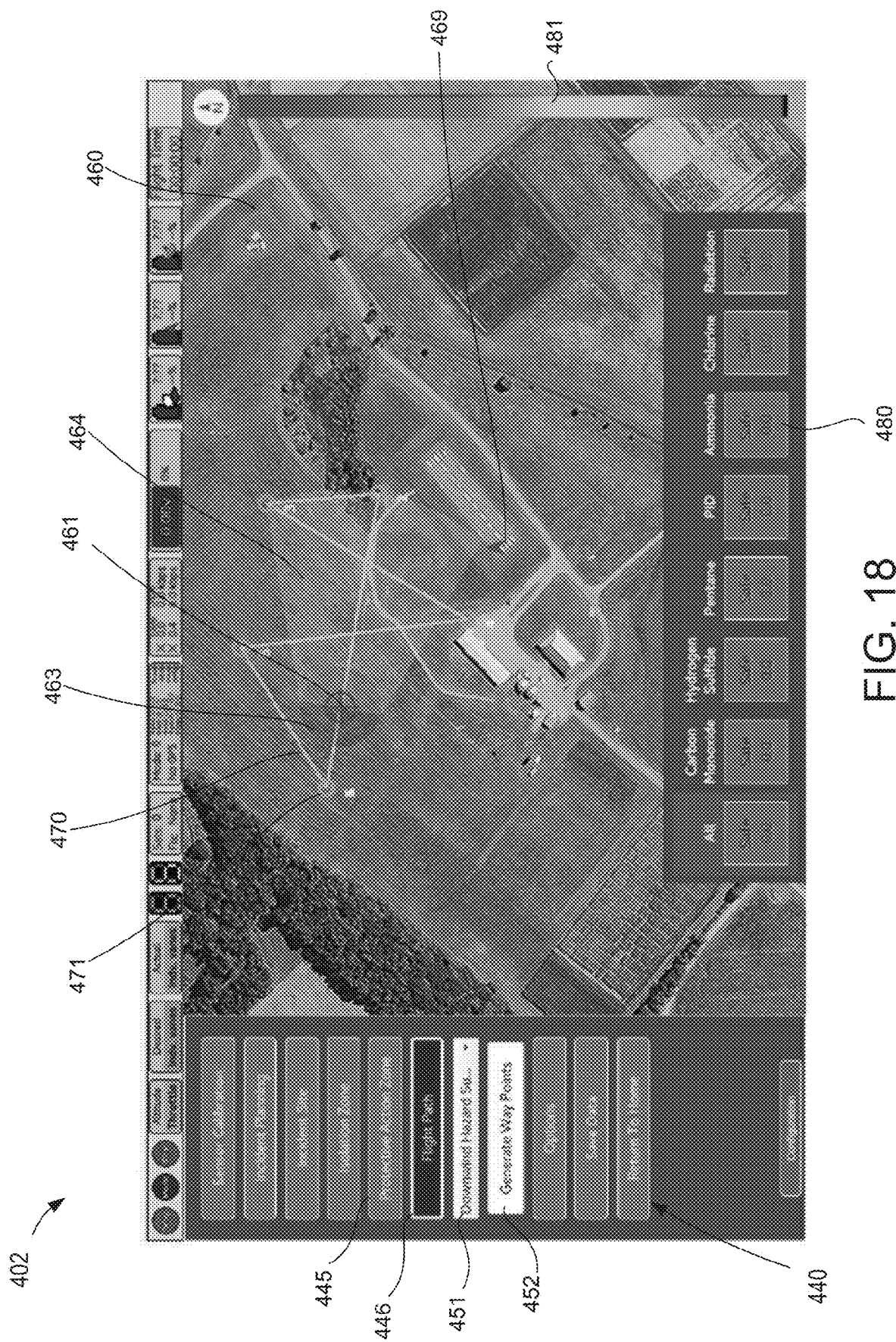
FIGS. 18 and 19 are images on a display monitor showing various flight paths displayed on a satellite aerial map or image, produced by a control system or methods according to an embodiment.

FIG. 18 shows details of the downwind hazard survey. The purpose of the downwind hazard survey is to maximize hazard data collection within the downwind area including but not limited to the PAZ. Unlike the PAZ survey which may not identify the extent of lateral dispersion of the hazard, the downwind hazard survey is designed to map the lateral and downwind dispersion of the hazard with up to five lateral surveys angled from the centerline. Because the flight path conforms to the downwind distance of the PAZ, the PAZ can be adjusted based on real-time measurements to enable more rapid completion of this survey. As shown, the system produces a series of waypoints 471 and flight segments to define the flight path 470. The flight path 470 begins upwind of the incident site and dissects the isolation and protective action zones to a point downwind of the protective action zone. Next, the flight path follows a zigzag pattern in the upwind and crosswind direction back to the starting point.

Better understanding the dispersion and movement of the hazard downwind of the incident can support several decisions including whether to approach the incident from other angles. Other advantages include confirming adequacy of the PAZ (lateral and downwind), or need to expand, decrease the size. The collected data can help determine lateral extent of hazard dispersion and migration and protection actions, such as evacuation or shelter-in-place. This survey can indicate rate of changing conditions and hazard migration as the first and last leg of the survey are repeated (beginning and end). This may aid in projecting whether the hazard will migrate further downwind.

Figure 19:
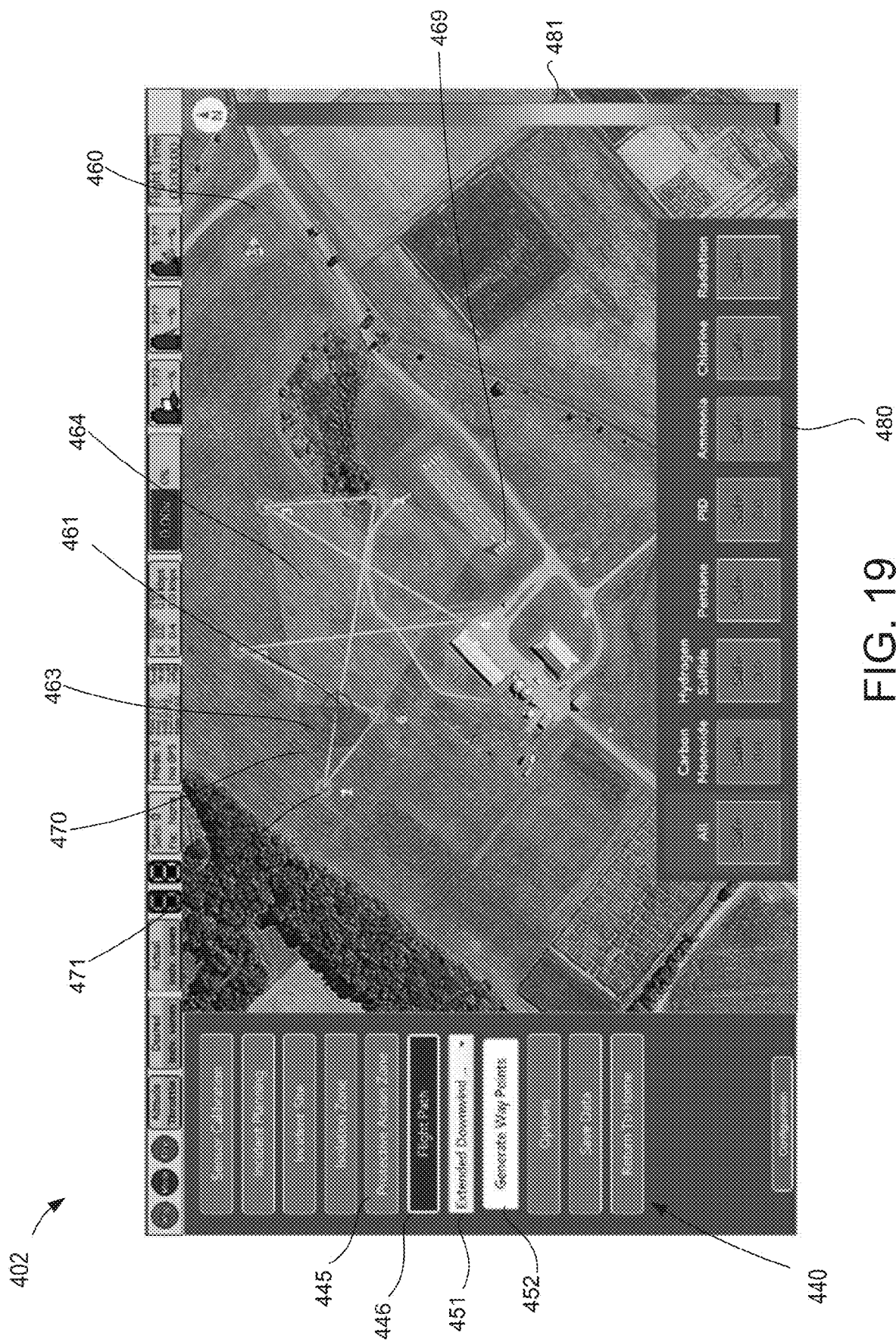
Figure 20:
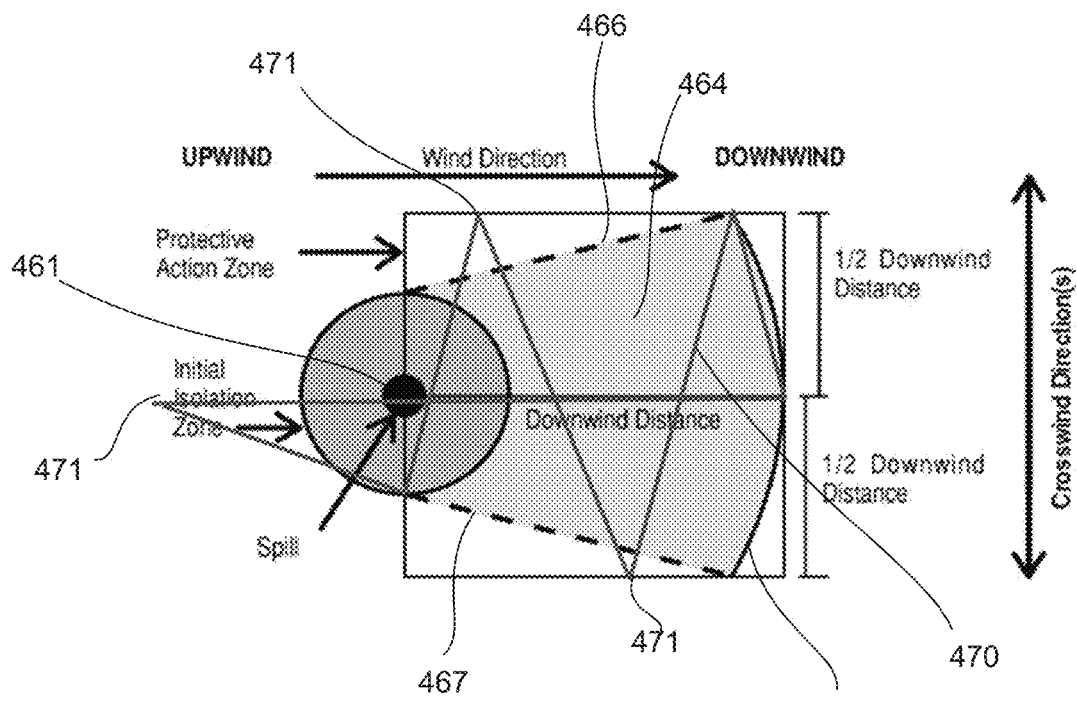
FIGS. 20 and 21 are schematic illustrations of various flight path associated with a protective action zone produced by a control system or methods according to an embodiment.

FIG. 19 shows details of the extended downwind hazard survey. The extended downwind hazard survey is similar to the downwind hazard survey flight path described above, except the path crosses the protective action zone and isolation zone one more time on its way back to the starting point. This survey is more likely accomplished with shorter downwind hazard distances, whereas the downwind hazard survey may be accomplished with longer distances requiring longer flight times.

Figure 22:
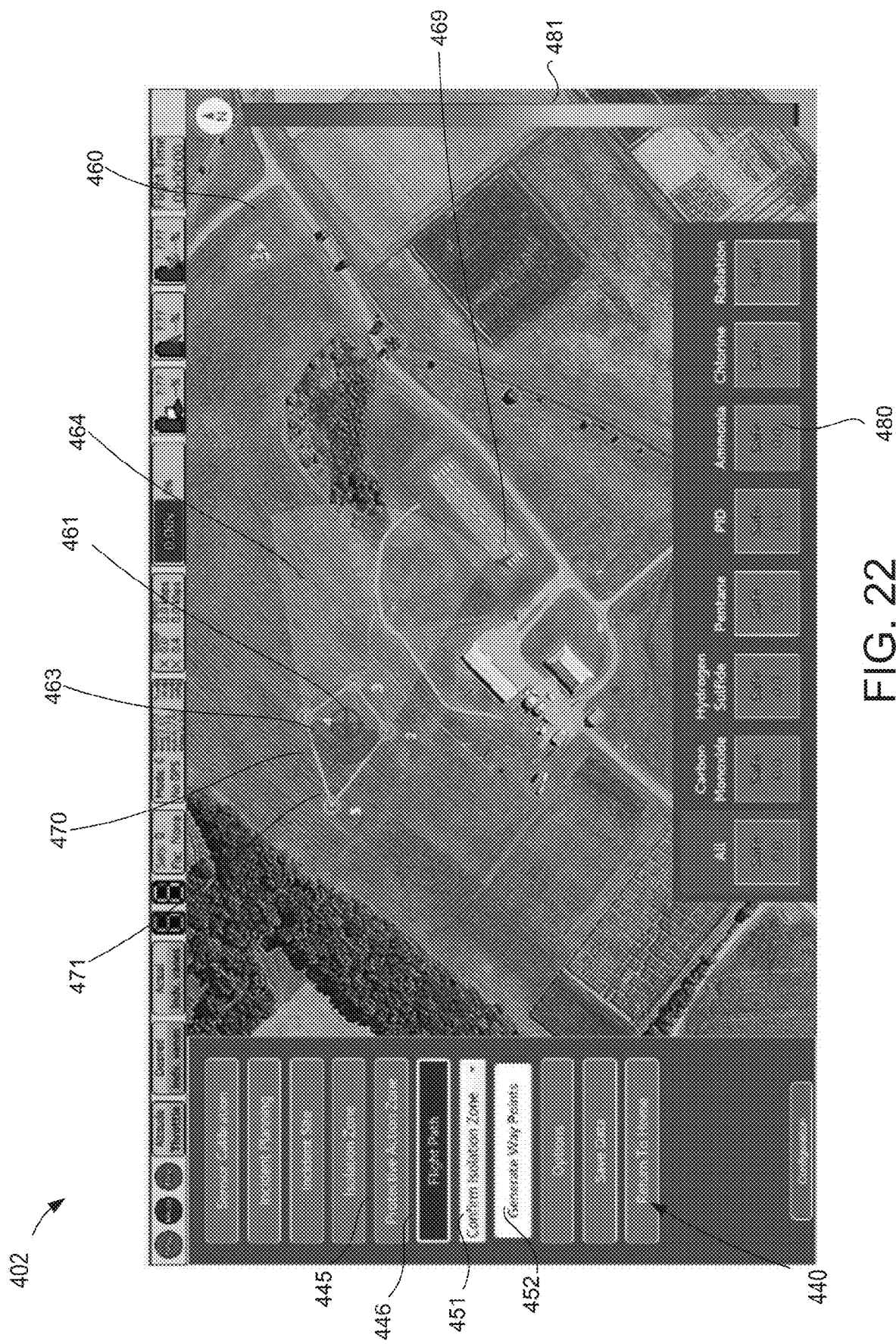
FIG. 22 is an image on a display monitor showing a flight path displayed on a satellite aerial map or image, produced by a control system or methods according to an embodiment.

FIG. 22 shows details of the confirm isolation zone survey. The purpose of the confirm isolation zone survey is to confirm that the size of the IZ is adequate to protect those outside the zone. It is based on a path that circumnavigates the IZ on the downwind side of the IZ. When used in combination with the IZ survey, it can complement the interior survey with an exterior survey. As shown, the system produces a series of waypoints 471 and flight segments to define the flight path 470. The flight path 470 begins at a point upwind of the isolation zone. The next waypoint is located at a lateral edge (crosswind) of the isolation zone, and then proceeds to a point directly downwind of the zone. From there, the path goes to the opposite lateral edge of the isolation zone and then returns to the starting point. One of the advantages of this survey is that it is the fastest survey and can confirm that the size of the IZ is adequate or needs to be expanded. Benefits of the confirm isolation zone survey include supporting decisions regarding whether to reducing the size of the IZ, whether the hazard is departing the IZ into the PAZ. This survey is also used to confirming safe upwind approaches and safe distances.

Figure 23A:
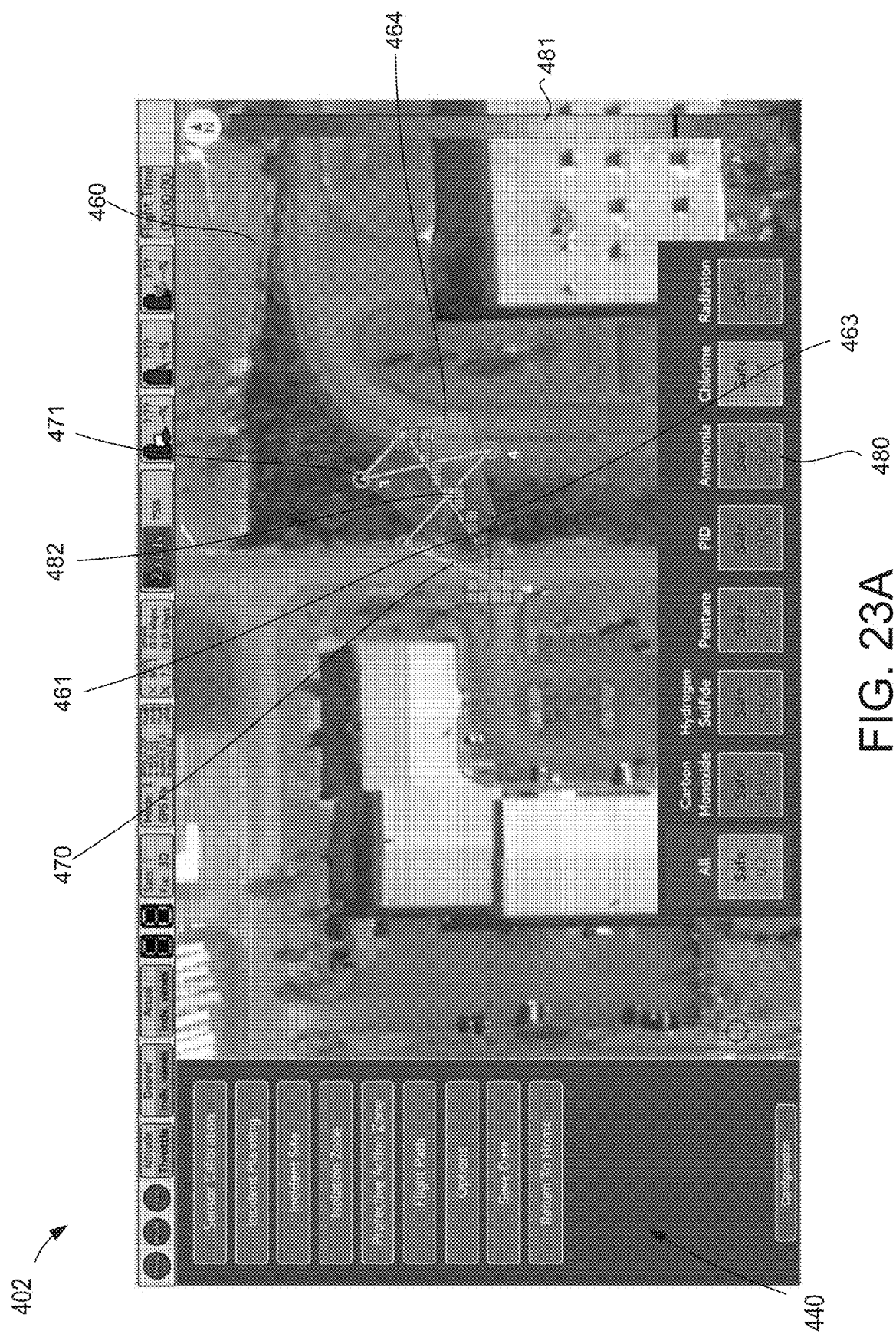
FIGS. 23A and 23B are images on a display monitor showing emissions data displayed on a satellite aerial map or image, produced by a display system or methods according to an embodiment.
Figure 23B:
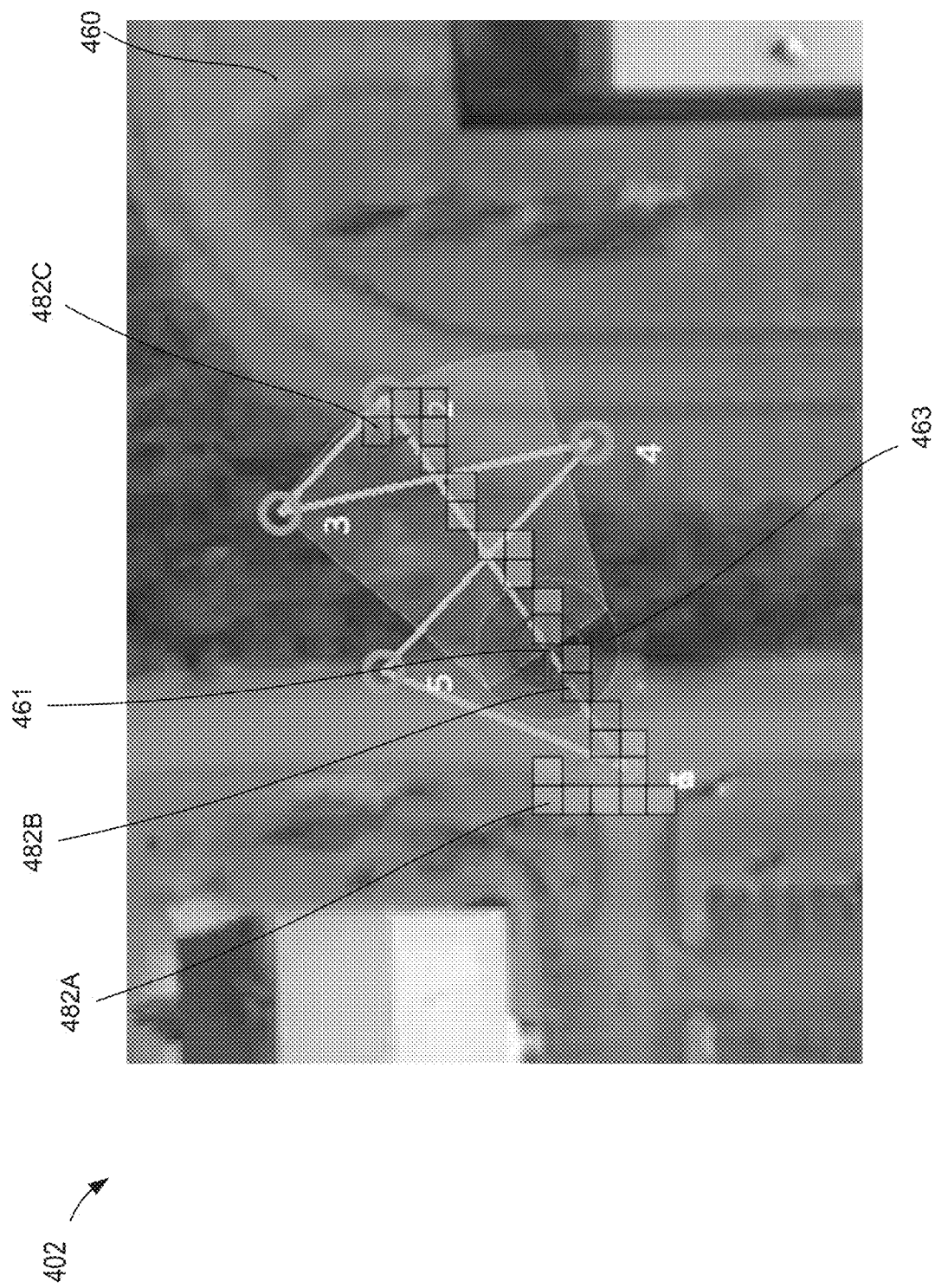

In embodiments, the system 100 or the system 200, in addition to producing the desired flight plan, also display the collected data on the display monitor 402. For example, FIGS. 23A and 23B show an image on the display monitor 402 that includes a set of emissions indicators 482 displayed on the satellite aerial map 460. In this example, the emissions data was collected using a downwind hazard survey, as described above. Each of the emissions indicators 482 occupies an area on the display that is scaled to correspond to a physical size within the protective action zone 464. For example, in some embodiments, each emission indicator (or "square") can represent an actual area of 10 square feet. As described above, the spatial resolution can be changed based on the desired UAV airspeed. Moreover, the emissions indicators can be displayed based on the geographic coordinates produced by the georectification module 223 and according to any of the methods described herein.

FIG. 23B is an enlarged view showing the emissions indicators 482, and more clearly shows the different colors for the indicators. As described above, the graphics module 224 can select a color associated with the concentration (or amount) of the hazardous material (or substance) and produce that color within the emissions indicator. Specifically, for this example, the different colors represent a hazard level associated with a range of concentration (or amount) for each measured hazardous material (or substance). The colored scale corresponds to an exposure level corresponding Acute Exposure Guideline Level (AEGL) for each hazardous material (or substance) sampled. Specifically, a red colored emissions indicator, such as the indicator 482B, indicates that at least one of the sampled materials has a concentration level (at the indicated spatial location) that is within a concentration range that corresponds to the AEGL-3 level. As the color scale moves towards orange, the emissions indicator can identify that at least one of the sampled materials has a concentration level (at the indicated spatial location) that is within a concentration range that corresponds to the AEGL-2 level. A more yellow colored emissions indicator, such as the indicator 482A, indicates that at least one of the sampled materials has a concentration level (at the indicated spatial location) that is within a concentration range that corresponds to the AEGL-1 level. Finally, a green colored emissions indicator, such as the indicator 482C, indicates that at least one of the sampled materials has a concentration level (at the indicated spatial location) that is within a concentration range that corresponds to less than the AEGL (e.g., safe level) for exposure.

This display and arrangement provides an efficient mechanism for evaluating the emissions indicators plotted (see e.g., FIG. 23) so that the user can quickly assess areas of safety within the measured zones. Moreover, the hazard level scale 481 is a single scale that standardizes the various different exposure level effects for all of the various materials for which measurements are taken. This increases situational awareness and allows the user to quickly assess whether any of the sampled hazardous materials (or substances) are above a certain safety threshold level.

In some embodiments, the systems and methods described herein can allow the display of the emissions indicators 482 to be filtered for faster analysis. For example, in some embodiments, the system also allows the user to display the emissions indicators 482 for only one hazardous material (or substance). Specifically, if the user selects a particular hazard along the sensor visualization ribbon 480, then the emissions indicators 482 will be displayed for only that hazard. As an example, if the user selects chlorine, then only the sampled data pertaining to chlorine concentration will be provided.

Figure 24:
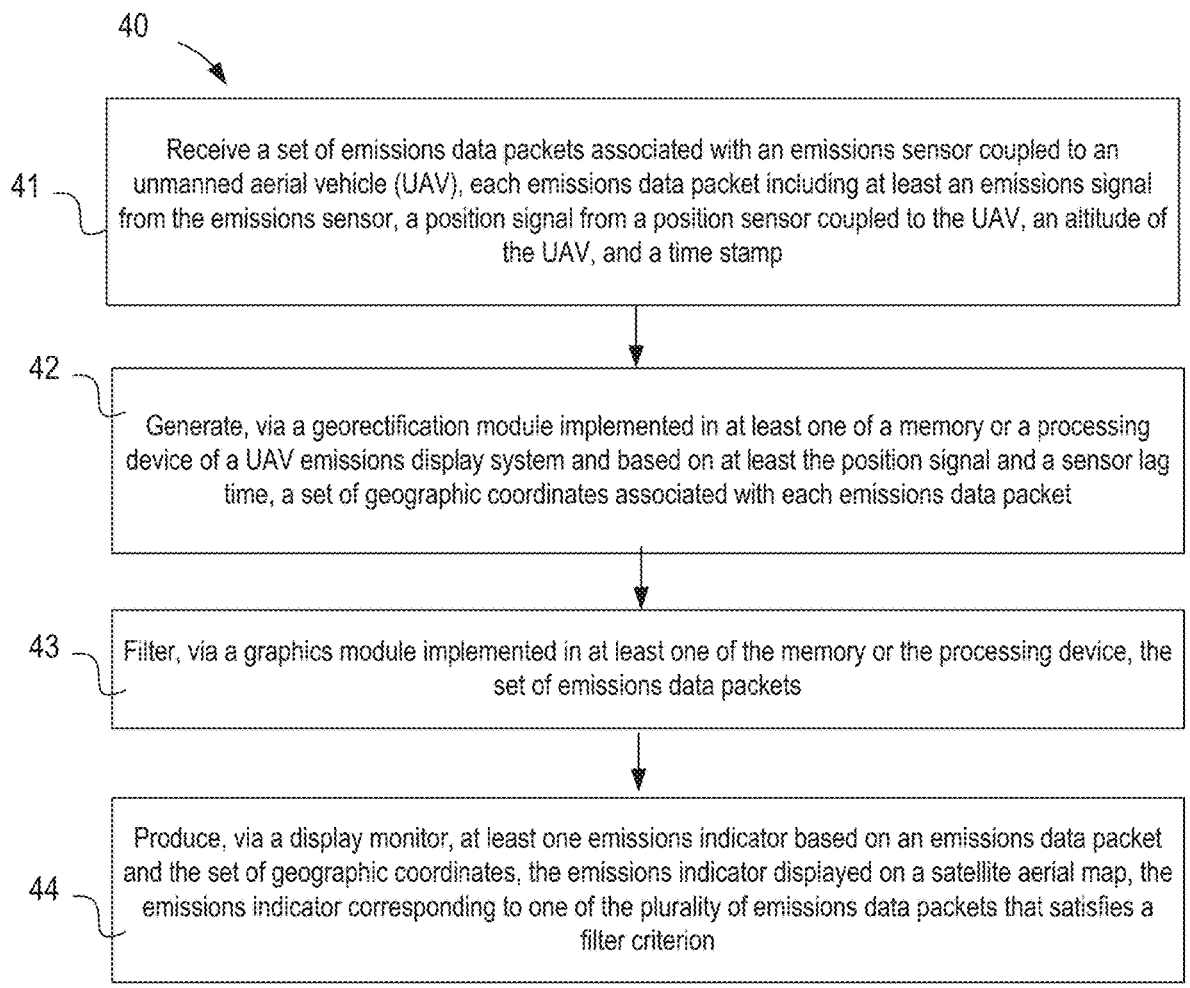
FIGS. 24 and 25 are flow charts of a computer-related method of filtering and displaying emissions information collected by a UAV, according to an embodiment.
Figure 25:
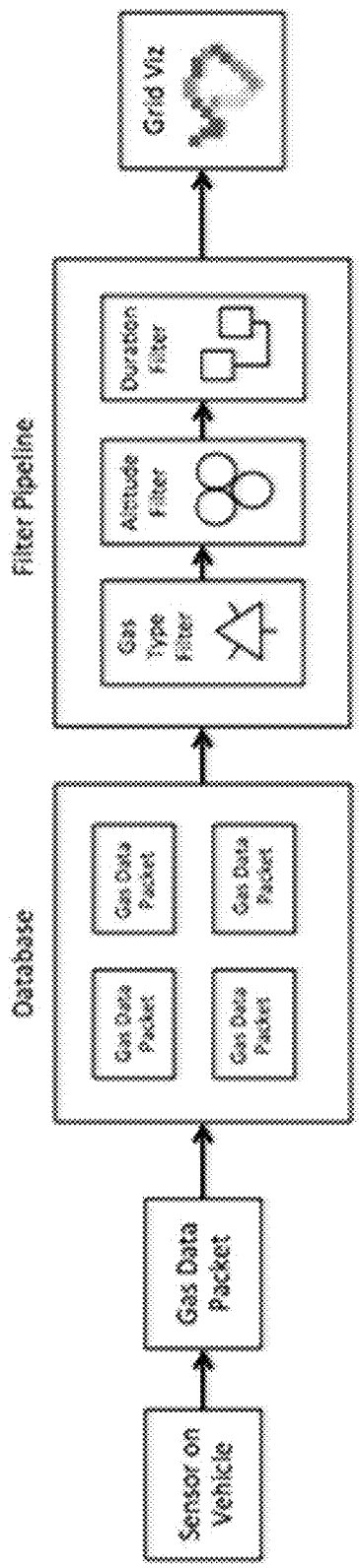

In other embodiments, the systems and methods described herein can filter the displayed emissions indicators 482 according to any suitable criterion, such as for example, the sampled altitude or the sample time. FIGS. 24 and 25 are a flow chart (FIG. 24) and a schematic flow diagram (FIG. 25) of a method 40 of filtering emissions indicators that are displayed on a satellite image map, according to an embodiment. The method 40 can be performed by the system 200 described above, or any other system described herein. The method includes receiving a set of emissions data packets associated with an emissions sensor coupled to an unmanned aerial vehicle (UAV), at 41. As described above, each emissions data packet includes a grouping of signals that correspond to a particular time, and each data packet can include, for example, a signal for each sensor, a time stamp, and one or more position signals (e.g., an altitude signal, a GPS location, and/or an airspeed reading).

Figure 26:
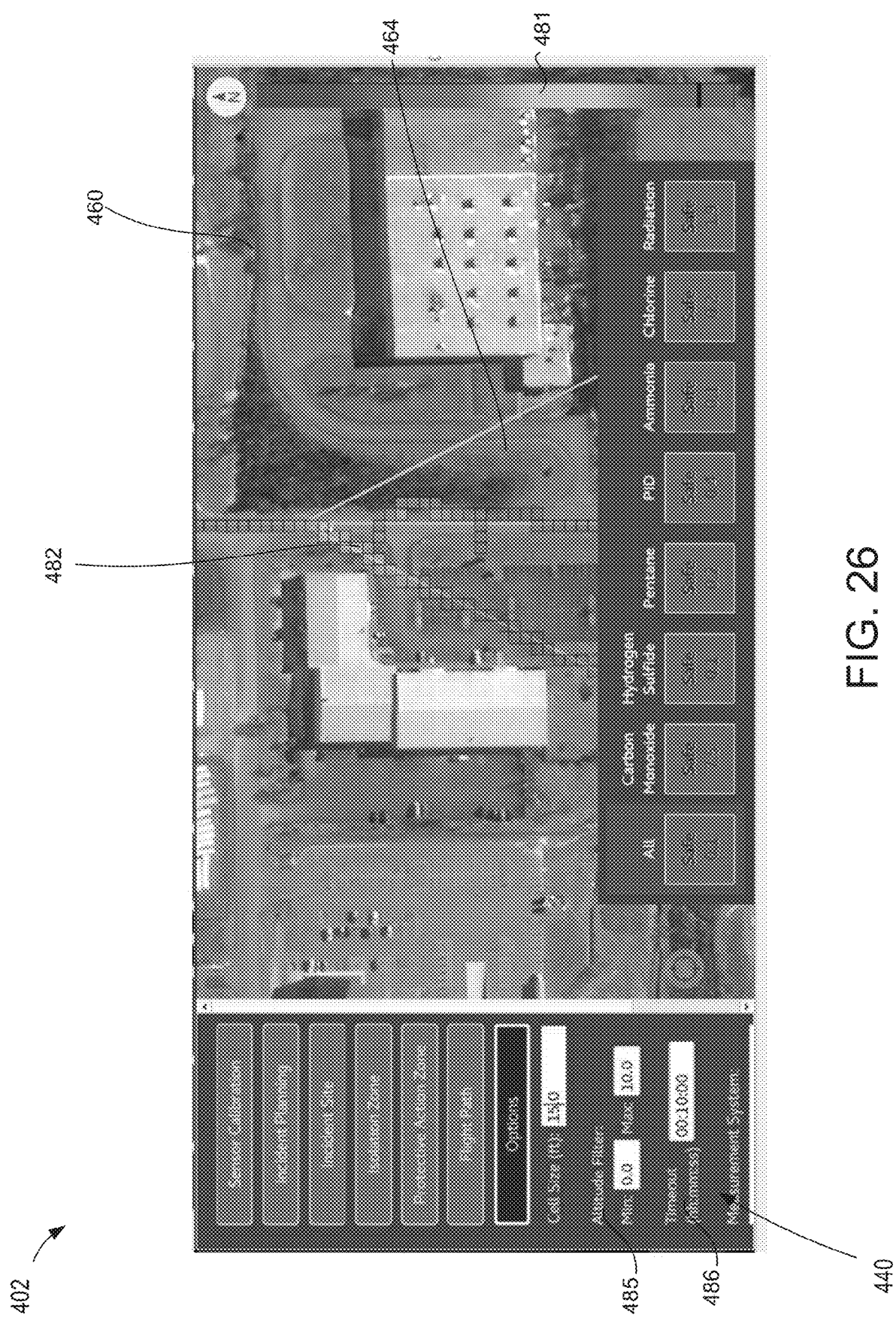
FIG. 26 is an image on a display monitor showing filtered emissions data displayed on a satellite aerial map or image, produced by a display system or methods according to an embodiment.

The method further includes generating a set of geographic coordinates associated with each emissions data packet based on at least the position signal and a sensor response time, at 42. The geographic coordinates can be generated via a georectification module implemented in at least one of a memory or a processing device of a UAV emissions display system, as described herein. The set of emissions data packets is then filtered based a filter criterion, at 43. The filtering can be performed by any of the application modules described herein, such as for example, the graphics module 224 described above. The filter criterion can be any suitable criterion. For example, as described above, in some embodiments, the data packets can be filtered based on the type of hazardous material (or substance). In this manner, the emissions indicators displayed can be specific to only the specific hazardous material (or substance) of interest. In other embodiments, the data packets can be filtered based on the altitude associated with each reading. For example, FIG. 26 shows an image including a set of emissions indicators 482 that are filtered to show only those indicators associated with a measurement at an altitude of less than 10 feet. The altitude filter can be selected via an altitude filter prompt 485. In other embodiments, the data packets can be filtered based on the time associated with each reading. In this manner "old" readings can be discarded to allow the responders to focus only on the most current readings. For example, FIG. 26 shows an image including a set of emissions indicators 482 that are filtered to show only those indicators associated with measurements that have been taken within the last 10 minutes. The time filter can be selected via a time filter prompt 486.

The method then includes producing, via a display monitor, at least one emissions indicator based on an emissions data packet that satisfies the filter criterion, at 44. As described above, the emissions indicator is displayed to scale on the satellite aerial map based on its set of geographic coordinates. In some embodiments, the method includes saving the data (either filtered or unfiltered) for later display. The data can be saved using the save data prompt 448 (see FIG. 11). The data can be saved in any suitable format, such as comma separated variable format and keyhole markup language format.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Figure 27:
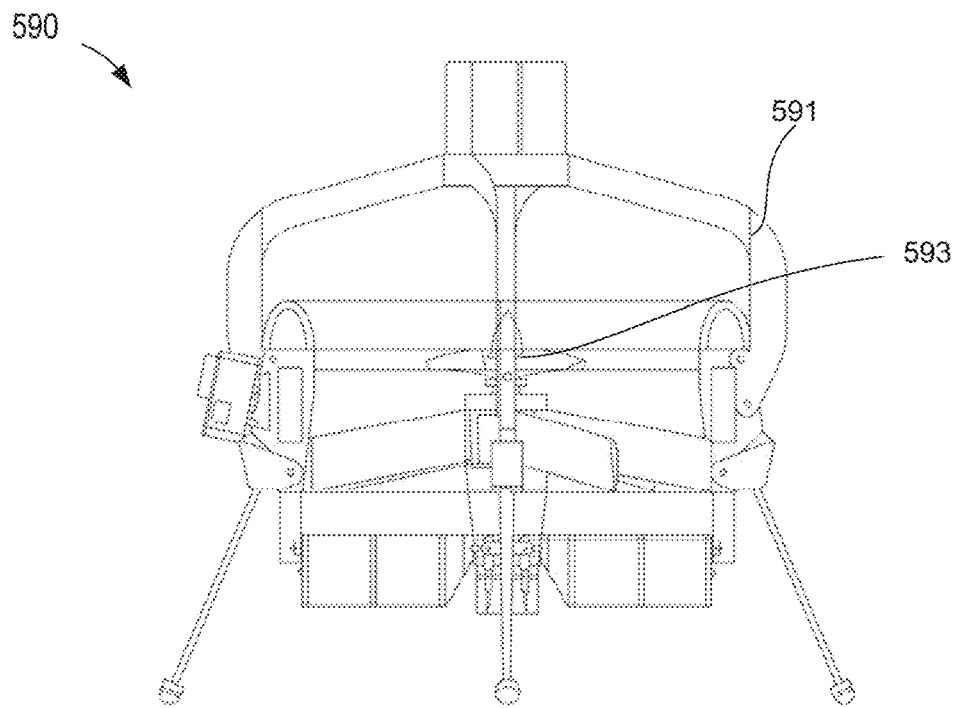
FIGS. 27 and 28 are a side cross-sectional view (FIG. 27) and a perspective view (FIG. 28) of a UAV including an emissions sensor assembly, according to an embodiment.
Figure 28:
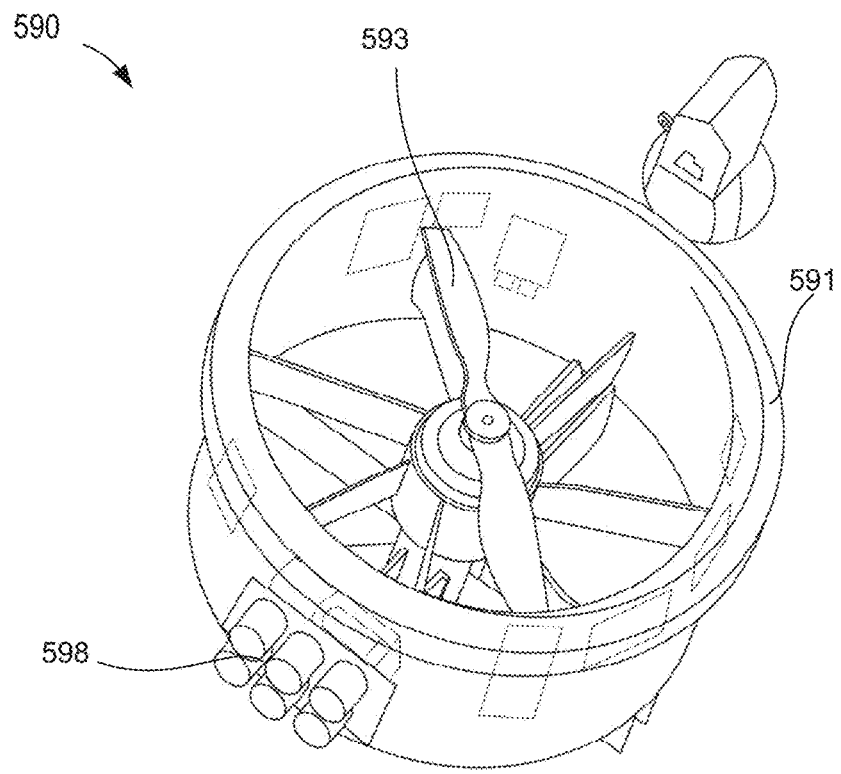

The methods and systems described herein can be used in conjunction with any suitable UAV. For example, FIGS. 27 and 28 show a UAV 590 as an example of a UAV that can be used in conjunction with and/or as a part of the systems and methods described herein. The UAV 590 is a ducted fan-type vehicle that includes a frame 591 that defines a duct, and a propeller 593. As shown in FIG. 28, the emissions sensor assembly 598 is coupled to the outside portion of the frame 591. The emissions sensor assembly 598 can include any suitable CBR sensors of the types shown and described herein. The UAV 590 also includes a position sensor assembly (not identified), of the types shown and described herein. In some embodiments, the UAV 590 can be the EDF-8 vehicle produced by Avid LLC.

The UAV 590 (or any of the UAVs described herein) can perform in accordance with any suitable specifications to perform the methods described herein. For example, in some embodiments, the UAV can be flown at altitude levels of up to 400 ft AGL (above ground level). In other embodiments, the UAV can be flown at altitudes up to 15,000 ft above sea level density altitude. In some embodiments, the maximum endurance of the vehicle is 30 minutes per battery charge.

Thus, as described herein, in some embodiments, the flight paths and/or speed warnings are based on a total flight time duration of 30 minutes, 25 minutes, 20 minutes, or less. In some embodiments, the UAV can include a command and control radio that can transmit 5 miles with a directional antenna. In some embodiments, the UAV can have an airspeed ranges from hover (~0 mph) to 35 mph. In some embodiments, the UAV can have a maximum rate of climb of 2 ft/sec at sea level for minimum weight configuration (2.5 lb) and a maximum rate of descent is −2 ft/sec.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the unmanned vehicles are described herein as being unmanned aerial vehicles, in other embodiments, the systems and methods described can be used in conjunction with any suitable unmanned vehicle. For example, in situations involving a hazardous incident at sea, the systems and methods described herein can be used with unmanned underwater vehicles. In other embodiments, the systems and methods described herein can be used with unmanned ground vehicles (e.g., unmanned rovers) or unmanned space flight vehicles. Thus, although the systems and methods are described herein as producing "flight path," in other embodiments, any of the systems and methods described herein can produce a "measurement path" suitable for the vehicle being used.

Although shown and described as producing images on a satellite aerial map, in other embodiments, any of the systems and methods described herein can produce the flight paths, waypoints, measurement zones, and/or emissions data on any suitable representation of the incident site. For example, in some embodiments, any of the systems and methods described herein can produce the flight paths, waypoints, measurement zones, and/or emissions data on a "street map" view of a region including the incident site. In other embodiments, any of the systems and methods described herein can produce the flight paths, waypoints, measurement zones, and/or emissions data on a topographic view of a region including the incident site. In yet other embodiments, any of the systems and methods described herein can produce the measurement paths, waypoints, measurement zones, and/or emissions data on an oceanic map, a flight map, a facility plan, a vessel plan, or other suitable map showing of a region including the incident site.

Although methods and systems are shown and described as producing geographical coordinates for various data in the form of a longitude and latitude coordinate set, in other embodiments, any of the systems and methods described herein can produce any suitable type of coordinate to allow for plotting and location of the data on the display monitors shown herein. For example, in some embodiments, any of the systems and methods described herein can produce a relative geographic positioning indicator or set of coordinates for any of the data described herein. In other embodiments, any of the systems and methods described herein can produce a vector positioning indicator (e.g., a magnitude and a direction) for any of the data described herein. Any of the geographical coordinates described herein can be produced to be compatible with a variety of mapping protocols, including Google Earth™ protocols.

Any of the radios, transmitters, receivers, and/or transceivers described herein can be operable to transmit, receive, repeat, and/or otherwise interact with electromagnetic signals. Electromagnetic signals can be of any suitable frequency. For example, the radios, transmitters, receivers, and transceivers can be operable to transmit and/or receive IEEE 802.11 signals, Bluetooth® signals, FM radio signals, AM radio signals, cellular telephone signals, satellite pager signals, RFID signals, GPS signals, and/or any other suitable electromagnetic signal.

Although various embodiments have been described as having particular features and/or combinations of components, other embodiments are possible having a combination of any features and/or components from any of embodiments where appropriate. For example, a system can include any of the features described above for the system 100 and the system 200. Thus, in some embodiments, a control system can perform control functions, flight path mapping functions, and emissions display functions.

What is claimed is:

1. An apparatus, comprising:
a display monitor; and
an unmanned aerial vehicle (UAV) control system operatively coupled to the display monitor, the UAV control system configured to be operatively coupled to a UAV to control any of an air speed, an altitude or a position of the UAV, the UAV including an emissions sensor and a position sensor, the UAV control system including:
an input module implemented in at least one of a memory or a processing device of the UAV control system, the input module configured to receive a first input and a second input, the first input associated with an incident location of an incident involving a hazardous substance, the second input associated with a measurement zone including the incident location;
a measurement zone module implemented in at least one of the memory or the processing device, the measurement zone module configured to generate a first set of geographic coordinates associated with a perimeter of the measurement zone based on the first input and the second input;
a flight path module implemented in at least one of the memory or the processing device, the flight path module configured to generate a second set of geographic coordinates associated with a flight path of the UAV based on the first input and the second input;
a sensor module implemented in at least one of the memory or the processing device, the sensor module configured to receive an emissions signal from the emissions sensor and a position signal from the position sensor;
a georectification module implemented in at least one of the memory or the processing device, the georectification module configured to generate a third set of geographic coordinates associated with the emissions signal based on at least the position signal and a sensor response time; and
a graphics module implemented in at least one of the memory or the processing device, the graphics module configured to display via the display monitor A) a satellite aerial map of a region including the incident location, B) a measurement zone image representing the measurement zone, the measurement zone image displayed on the satellite aerial map, and C) a plurality of emissions indicators on the satellite aerial map, the plurality of emissions indicators based on the emissions signal and the third set of geographic coordinates, the graphics module configured to adjust a size of each of the plurality of emissions indicators to correspond to a spatial resolution associated with the air speed of the UAV.

2. The apparatus of claim 1, wherein:
the second input includes a size of the measurement zone and a wind direction of the incident location; and
the input module is configured to receive the second input in response to an input prompt displayed via the display monitor.

3. The apparatus of claim 1, wherein:
the flight path module is configured to generate the second set of geographic coordinates associated with a plurality of waypoints, the flight path module configured to generate a plurality of flight segments to define the flight path, each flight segment from the plurality of flight segments connecting at least two waypoints from the plurality of waypoints.

4. The apparatus of claim 3, wherein:
the second input includes a size of the measurement zone and a wind direction of the incident location;
the perimeter of the measurement zone includes a first edge, a second edge, and an arc downwind from the incident location that connects the first edge and the second edge, the arc centered at the incident location and having an arc radius associated with the size; and
the flight path module is configured to generate the plurality of waypoints to include a first waypoint from the plurality of waypoints on the arc, a second waypoint from the plurality of waypoints on the first edge, and a third waypoint from the plurality of waypoints on the second edge.

5. The apparatus of claim 1, wherein:
the second input includes any of an identification of the hazardous substance, an amount of the hazardous substance, a wind direction, and a time of day;
the input module is configured to receive a first portion of the second input in response to an input prompt displayed via the display monitor and a second portion of the second input from a remote computing device; and
the measurement zone module is configured to determine a downwind distance associated with the hazardous substance based on the second input.

6. The apparatus of claim 1, wherein an emissions indicator from the plurality of emissions indicators includes a color associated with a concentration of the hazardous substance based on the emissions signal.

7. The apparatus of claim 1, wherein:
the input module is configured to receive a third input associated with one of a desired air speed of the UAV or a desired spatial resolution of the plurality of emissions indicators; and
the graphics module is configured to adjust the size of each of the plurality of emissions indicators based at least in part on the third input.

8. A non-transitory storage medium that stores a program causing a processor to execute a method of producing for emissions data from an unmanned aerial vehicle (UAV), the method comprising:
receiving a first input associated with an incident location of an incident involving a hazardous substance;
receiving a second input associated with a measurement zone including the incident location;

receiving a third input associated with at least one of an air speed of the UAV or a desired spatial resolution of a plurality of emissions indicators;

producing, via a display monitor, a measurement zone image representing the measurement zone, the measurement zone image displayed on a satellite aerial map of a region including the incident location, the measurement zone image being scaled to the satellite aerial map;

producing, via the display monitor, a flight path of the UAV based on the first input and the second input, the flight path displayed on the satellite aerial map of the region;

receiving from an emissions sensor coupled to the UAV an emissions signal associated with an amount of the hazardous substances;

receiving, from a position sensor coupled to the UAV, a position of the UAV;

determining, based on at least the position of the UAV and a response time of the emissions sensor, a set of geographic coordinates associated with the emissions signal; and producing, via the display monitor, the plurality of emissions indicators on the satellite aerial map based on the set of geographic coordinates, a size of each of the plurality of emissions indicators being adjusted to correspond to the desired spatial resolution and the air speed of the UAV.

9. The non-transitory storage medium of claim 8, wherein:
the set of geographic coordinates is a first set of geographic coordinates;
the second input includes a size of the measurement zone and a wind direction of the incident location; and
the producing the measurement zone image includes:
determining, based on the size and the wind direction, a second set of geographic coordinates associated with a perimeter of the measurement zone; and
displaying, via the display monitor, the perimeter of the measurement zone on the satellite aerial map.

10. The non-transitory storage medium of claim 8, wherein:
the set of geographic coordinates is a first set of geographic coordinates;
the second input includes a size of the measurement zone and a wind direction of the incident location; and
the producing the flight path includes:
determining, based on the size of the measurement zone and the wind direction, a second set of geographic coordinates associated with a plurality of waypoints;
determining a plurality of flight segments to define the flight path, each flight segment from the plurality of flight segments connecting at least two waypoints from the plurality of waypoints; and
displaying, via the display monitor, the plurality of flight segments on the satellite aerial map.

11. The non-transitory storage medium of claim 10, wherein the set of the producing the flight path further includes:
determining, based on the size of the measurement zone and the wind direction, a third set of geographic coordinates associated with a perimeter of the measurement zone, the perimeter including a first edge, a second edge, and an arc downwind from the incident location that connects the first edge and the second edge, the plurality of waypoints determined such that a first waypoint from the plurality of waypoints is on the arc, a second waypoint from the plurality of waypoints is on the first edge, and a third waypoint from the plurality of waypoints is on the second edge.

12. The non-transitory storage medium of claim 8, wherein:
the measurement zone includes an isolation zone surrounding the incident location;
the second input includes an identification of the hazardous substance and an amount of the hazardous substance; and
the producing the measurement zone image includes determining a size of the isolation zone.

13. The non-transitory storage medium of claim 8, wherein:
the second input includes a size of the measurement zone and a wind direction of the incident location;
the measurement zone is an isolation zone, the isolation zone being a circle about the incident location and the size of the measurement zone includes a radius of the isolation zone; and
the producing the flight path includes:
determining, based on the size of the isolation zone and the wind direction, a set of geographic coordinates associated with a plurality of waypoints;
determining a flight segment of the flight path, the flight segment connecting at least two waypoints from the plurality of waypoints; and
the flight segment being tangent to the isolation zone.

14. The non-transitory storage medium of claim 8, wherein:
the set of geographic coordinates is a first set of geographic coordinates;
the measurement zone includes a protective action zone associated with the incident location:
the second input includes an identification of the hazardous substance, an amount of the hazardous substance, a wind direction, and a time of day; and
the producing the measurement zone image includes:
determining, based on the second input, a downwind distance associated with the hazardous substance;
determining a second set of geographic coordinates associated with a perimeter of the protective action zone, the perimeter including a center line aligned with the wind direction; and
displaying the perimeter of the measurement zone on the satellite aerial map.

15. The non-transitory storage medium of claim 8, further comprising:
determining a flight distance based on the flight path;
determining a minimum air speed threshold based on the flight distance and a flight duration; and
producing, via the display monitor, a notification associated with the minimum air speed threshold.

16. The non-transitory storage medium of claim 15, wherein the notification is a first notification, the method further comprising:
determining a maximum air speed threshold based on the response time of the emissions sensor and the desired spatial resolution of the plurality of emissions indicators; and
producing, via the display monitor, a second notification associated with the maximum air speed threshold.

17. The non-transitory storage medium of claim 8, wherein the method of producing emissions data further comprises:

producing, via the display monitor, a notification that the air speed of the UAV has exceeded a maximum air speed threshold.

18. The non-transitory storage medium of claim 8, wherein:
the displaying the plurality of emissions indicators includes selecting for an emissions indicator from the plurality of emissions indicators a color associated with a concentration of the hazardous substance based on the emissions signal.

19. A non-transitory storage medium that stores a program causing a processor to execute a method of producing a plurality of emissions indicators and a maximum speed threshold for an unmanned aerial vehicle (UAV), the UAV including a position sensor and an emissions sensor, the emissions sensor configured to produce an emissions signal associated with a concentration of a hazardous substance, the method comprising:
receiving a first input associated with an incident location of an incident involving the hazardous substance;
receiving a second input associated with a measurement zone surrounding the incident location;
receiving a third input associated with a desired spatial resolution of the plurality of emissions indicators;
producing a flight path of the UAV using the first input and the second input, the flight path displayed on a satellite aerial map of a region including the incident location;
determining the maximum air speed threshold for the UAV using a sensor response time of the emissions sensor and the desired spatial resolution of the plurality of emissions indicators;
receiving a position signal associated with a position of the UAV from the position sensor;
receiving the emissions signal from the emissions sensor;
displaying the plurality of emissions indicators on the satellite aerial map based on the position signal and the emissions signal, a size of each of the plurality of emissions indicators being adjusted to correspond to the desired spatial resolution and an air speed of the UAV; and
producing a notification on a condition that the air speed of the UAV has exceeded the maximum air speed threshold for the UAV.

20. The non-transitory storage medium of claim 19, wherein:
the displaying the plurality of emissions indicators includes selecting for an emissions indicator from the plurality of emissions indicators a color associated with a concentration of the hazardous substance based on the emissions signal.

* * * * *

UNITED STATES PATENT AND TRADEMARK OFFICE
CERTIFICATE OF CORRECTION

PATENT NO. : 11,922,821 B2
APPLICATION NO. : 17/367945
DATED : March 5, 2024
INVENTOR(S) : Robert K. Campbell It is certified that error appears in the above-identified patent and that said Letters Patent is hereby corrected as shown below:

In the Claims

Claim 8, Line 2, Column 32, Line 61: delete "for" at the end of the line; and
Claim 8, Line 24, Column 33, Line 17: change "substances" to --substance--.

Signed and Sealed this
Fourteenth Day of May, 2024

Katherine Kelly Vidal
*Director of the United States Patent and Trademark Office*